United States Patent
Hedrick et al.

(10) Patent No.: US 6,737,252 B2
(45) Date of Patent: May 18, 2004

(54) 7 TRANSMEMBRANE RECEPTOR FAMILY MEMBER BLRX

(75) Inventors: Joseph A. Hedrick, Plainsboro, NJ (US); Bernhard Homey, Dusseldorf (DE); Alain Vicari, Lyons (FR); Monica L. Zepeda, San Diego, CA (US); Albert Zlotnik, Palo Alto, CA (US)

(73) Assignees: Schering Corporation, Kenilworth, NJ (US); Canji, Inc., San Diego, CA (US)

( * ) Notice: Subject to any disclaimer, the term of this patent is extended or adjusted under 35 U.S.C. 154(b) by 0 days.

(21) Appl. No.: 09/910,695

(22) Filed: Jul. 20, 2001

(65) Prior Publication Data

US 2003/0166052 A1 Sep. 4, 2003

Related U.S. Application Data

(63) Continuation-in-part of application No. 09/122,585, filed on Jul. 24, 1998, now abandoned.
(60) Provisional application No. 60/053,693, filed on Jul. 25, 1997.

(51) Int. Cl.$^7$ .......................... C12N 15/12; C12N 5/10; C12N 15/63

(52) U.S. Cl. .................... 435/69.1; 435/71.1; 435/71.2; 435/471; 435/325; 435/320.1; 435/252.3; 435/254.11; 536/23.5; 536/24.3; 536/24.31

(58) Field of Search .................................. 530/350, 351; 536/23.1, 23.5, 24.3, 24.31; 435/69.1, 71.1, 71.2, 471, 325, 320.1, 252.3, 254.11

(56) References Cited

U.S. PATENT DOCUMENTS

| | | | |
|---|---|---|---|
| 5,248,666 A | 9/1993 | Twardzik et al. | |
| 5,262,522 A | 11/1993 | Gearing | |
| 5,932,445 A | 8/1999 | Lal et al. | |

FOREIGN PATENT DOCUMENTS

| | | |
|---|---|---|
| WO | WO 94/12519 | 6/1994 |
| WO | WO 94/12635 | 6/1994 |
| WO | WO 95/03318 | 2/1995 |
| WO | WO 95/04158 | 2/1995 |
| WO | WO 95/10538 | 4/1995 |
| WO | WO 96/05226 | 2/1996 |
| WO | WO 96/13587 | 5/1996 |
| WO | WO 96/23225 | 8/1996 |
| WO | WO 96/30406 | 10/1996 |
| WO | WO 96/37621 | 11/1996 |
| WO | WO 96/39434 | 12/1996 |
| WO | WO 96/39438 | 12/1996 |
| WO | WO 96/40040 | 12/1996 |

OTHER PUBLICATIONS

Skolnick et al. Nature Biotechnology. vol. 18, pp. 283–287, 2000.*
Mikayama et al. Proc. Natl. Acad. Sci. USA vol. 90, pp. 10056–10060, 1993.*
Voct et al. Biochemistry. John Wiley & Sons, Inc. pp. 126–128, and 228–236, 1990.*
Anne L. Angiolillo, et al., *Ann. NY Acad. Sci.*, 795:158–167, Oct. 31, 1996. "A Role for the Interferon–Inducible Protein 10 in Inhibition of Angiogenesis by Interleukin–12".
Anne L. Angiolillo, et al., *J. Exp. Med.*, 182(1):155–162, Jul. 1, 1995. "Human Interferon–inducible Protein 10 is a Potent Inhibitor of Angiogenesis In Vivo".
Douglas A. Arenberg, et al., *J. Exp. Med.*, 184(3):981–992, Sep. 1, 1996. "Interferon–γ–inducible Protein 10 (IP–10) is an Angiostatic Factor That Inhibits Human Non–small Cell Lung Cancer (NSCLC) Tumorigenesis and Spontaneous Metastases".
Masataka Baba, et al., *J. Biol. Chem.*, 272(23(:14893–14898, Jun. 6, 1997. "Identification of CCR6, the Specific Receptor for a Novel Lymphocyte–directed CC Chemokine LARC".
Ian Clark–Lewis, et al., *J. Biol. Chem.*, 269(23):16075–16081, Jun. 10, 1994. "Structural Requirements for Interleukin–8 Function Identified by Design Analogs and CXC Chemokine Hybrids".
Brian Cunningham, et al., *Science*, 244: 1081–1985, Jun. 2, 1989. "High–Resolution Epitope Mapping of hGH–Receptor Interactions by Alanine–Scanning Mutagenesis".
Joshua M. Farber, *Biochem. Biophys. Res. Comm.*, 192(1):223–230, Apr. 15, 1993. "HuMIG: A New Human Member of the Chemokine Family of Cytokines".
Joshua M. Farber, *Proc. Natl. Acad. Sci. USA*, 87:5238–5242, Jul. 1990. "A macrophage mRNA selectively induced by γ–interferon encodes a member of the platelet factor 4 family of cytokines".
Reinhold Förster, et al., *Cell*, 87(6):1037–1047, Dec. 13, 1996. "A Putative Chemokine Receptor, BLR1 Directs B cell Migration to Defined Lymphoid Organs and Secific Anatomic Compartments of the Spleen".
I. Gantz, et al., GenBank, Accession No. L42324, Aug. 6, 1997. Definition: "*Homo sapiens* (clone GPCR W) G protein–linked receptor gene (GPCR) gene, 5' end of cds."
I. Gantz, et al., GenBank, Accession No. L42326, Aug. 6, 1997. Definition: "*Canis familiaris* (clone GPCR W) DNA fragment."

(List continued on next page.)

Primary Examiner—Prema Mertz
(74) Attorney, Agent, or Firm—Edwin P. Ching; Sheela Mohan-Peterson; Sandy Zaradic

(57) ABSTRACT

Novel chemokines and 7 transmembrane receptors from mammals, reagents related thereto, including purified proteins, specific antibodies, and nucleic acids encoding the chemokines and receptors are disclosed. Methods of using the chemokines, receptors, reagents and diagnostic kits are also provided.

16 Claims, 11 Drawing Sheets

OTHER PUBLICATIONS

David George, et al., *Macromolecular Sequencing and Synthesis: Selected Methods and Applications*, 127–149, chapter 12, 1998.

J. Hedrick, et al., GenBank, Accession No. AF001979, Nov. 20, 1997. Definition: "*Homo sapiens* beta chemokine mRNA, complete cds."

J. Hedrick, et al., GenBank, Accession No. AF001980, Nov. 20, 1997. Definition: "*Mus musculus* beta chemokine mRNA, complete cds."

Kunio Hieshima, et al., *J. Biol. Chem.*, 272(9):5846–5853, Feb. 28, 1997. "Molecular Cloning of a Novel Human CC Chemokine Liver and Activation–regulated Chemokine (LARC) Expressed in Liver".

Robert Hromas, et al., *Blood*, 89(9):3315–3322, May 1, 1997. Cloning and Characterization of Exodus, a Novel β–Chemokine.

R. Hromas, et al., GenBank, Accession No. U88320, Dec. 18, 1997. Definition: "Human beta chemokine Exodus–2 mRNA, complete cds."

R. Hromas, et al., GenBank, Accession No. U88322, Jun. 1, 1998. Definition: "*Mus musculus* beta chemokine Exodus 2–mRNA, complete cds."

Marcel Loetscher, et al., *J. Experimental Medicine*, 184:963–969, Sep. 1996. "Chemokine Receptor Specific for IP 10 and Mig: Structure, Function and Expression in Activated T–Lymphocytes".

Andrew D. Luster, et al., *Nature*, 315:672–676, Jun. 20, 1985. "γ–Interferon transcriptionally regulates an early–response gene containing homology to platelet proteins".

M. Marra, et al., GenBank Accession No. AA177904, Feb. 16, 1997. Definition: "mt05c02.r1 Soares mouse 3NbMS *Mus musculus* cDNA clone IMAGE:620265 5'; mRNA sequence."

M. Marra, et al., GenBank, Accession No. AA185904, Jan. 9, 1997. Definition "mu54a03.r1 Soares mouse lymph node NbMLN *Mus musculus* cDNA clone IMAGE:643180 5', mRNA sequence."

M. Marra, et al., GenBank, Accession No. AA423677, Oct. 16, 1997. Definition "ve77d08.r1 Soares mouse mammary gland NbMMG *Mus musculus* cDNA clone IMAGE:832239 5' similar to TR:G1066731 G1066731 G Protein–Linked Receptor;, mRNA sequence."

M. Marra, et al., GenBank, Accession No. AA466996, Jun. 11, 1997. Definition: "ve71a08.r1 Soares mouse mammary gland NbMMG *Mus musculus* cDNA clone IMAGE:831638 5', mRNA sequence."

Matsuoka, et al., *Biochemical and Biophysical Research Communications*, 194(1):504–511, Jul. 15, 1993. "Identification of Novel Members of G–Protein Coupled Receptor Superfamily Expressed in Bovine Taste Tissue".

NCI–CGAP (Robert Strausberg), GenBank, Accession No. AA258793, Aug. 13, 1997. Definition "zs32c03.s1 NCI_CGAP_GCB1 *Homo sapiens* cDNA clone IMAGE:686884 3' similar to TR:G1066731 G1066731 G Protein–Linked Receptor;, mRNA sequence."

NCI–CGAP (Robert Strausberg), GenBank, Accession No. AA258898, Aug. 13, 1997. Definition "zs32c03.r1 NCI_CGAP_GCB1 *Homo sapiens* cDNA clone IMAGE:686884 5' similar to TR:G1066731 G1066731 G Protein–Linked Receptor;, mRNA sequence."

Yoshihiro Ohmori & Thomas A. Hamilton, *Biochem. Biophys. Res. Commun.*, 168(3):1261–1267, May 16, 1990. "A Macrophage LPS–Inducible Early Gene Encodes the Murine Homolog of IP–10".

A.H. Sams, et al., *Leukemia*, 10(5):757–765, May 1996. "Human recombinant interferon–inducible protein–10 inhibits the proliferation of normal and acute myelogenous leukemia progenitors".

Cecilia Sgadari, et al., *Blood*, 89(8):2635–2643, Apr. 15, 1997. "Mig, the Monokine Induced By Interferon–γ, Promotes Tumor Necrosis in Vivo".

Cecilia Sgadari, et al., *Proc. Natl. Acad. Sci. USA*, 93(24):13791–13796, Nov. 26, 1996. "Interferon–inducible protein–10 identified as a mediator of tumor necrosis in vivo".

R.M. Streiter, et al., *Biochem. Biophys. Res. Commun.*, 210(1):51–57, May 5, 1995. "Interferon γ–Inducible Protein 10 (IP–10), A Member of the C–X–C Chemokine Family, is an Inhibitor of Angiogenesis".

Robert M. Streiter, et al., *J. Leuk. Biol.*, 57:752–762, May 1995. "Role of C–X–C chemokines as regulators of angiogenesis in lung cancer".

S. Tanabe, et al., GenBank, Accession No. AF006637, Jun. 22, 1997. Definition: "*Mus musculus* beta–chemokine TCA4 mRNA, complete cds."

Padmavathy Vanguri & Joshua M. Farber, *J. of Biol. Chem.*, 265(25): 15049–15057, Sep. 5, 1990. "Identification of CRG–2".

\* cited by examiner

```
GTTAAACCAC ACTATTC ATG CAA AAG GGT GTA GGG TTA CTG AGG ACA GTT          50
                   Met Gln Lys Gly Val Gly Leu Leu Arg Thr Val
                    1               5                    10

CCC TTG GTA CCT TCA GTC TCT GGT CAG ATT GAC CTT TTG GTA CTG TGT          98
Pro Leu Val Pro Ser Val Ser Gly Gln Ile Asp Leu Leu Val Leu Cys
            15              20                  25

ATG TGT ATA AAA ACG ACT ACT CCT CAT ATA TTT ATT TCT GAT TAT AAG         146
Met Cys Ile Lys Thr Thr Thr Pro His Ile Phe Ile Ser Asp Tyr Lys
        30              35                  40

ATA ATA TAT TCT GGA AAA CAC TGG AAA ATA CAT                             179
Ile Ile Tyr Ser Gly Lys His Trp Lys Ile His
        45              50
```

FIGURE 1

```
GTCTAAAACA AAATACAACA TTTCTTAAAT ACACTGTTTC CAGAAAGAGC TATTTTAACA        60

GAAGCAACTC AAAGATATCC CTTCGACAGA AGTGGAAGTG CTGAAAAATG CTCATCTCTC       120

ACACAGACTT TGATGGACA GGAGTTTCTA AGTATCATGC CTACCAACAA GCTGTAAA         178
```

| | | | | | | | | | | | | | | | | |
|---|---|---|---|---|---|---|---|---|---|---|---|---|---|---|---|---|
| ATG | ATC | ACC | CTG | AAC | AAT | CAA | GAT | CAA | CCT | GTC | CCT | TTT | AAC | AGC | TCA | 226 |
| Met | Ile | Thr | Leu | Asn | Asn | Gln | Asp | Gln | Pro | Val | Pro | Phe | Asn | Ser | Ser | |
| 1 | | | | 5 | | | | | 10 | | | | | 15 | | |
| CAT | CCA | GAT | GAA | TAC | AAA | ATT | GCA | GCC | CTT | GTC | TTC | TAT | AGC | TGT | ATC | 274 |
| His | Pro | Asp | Glu | Tyr | Lys | Ile | Ala | Ala | Leu | Val | Phe | Tyr | Ser | Cys | Ile | |
| | | | 20 | | | | | 25 | | | | | 30 | | | |
| TTC | ATA | ATT | GGA | TTA | TTT | GTT | AAC | ATC | ACT | GCA | TTA | TGG | GTT | TTC | AGT | 322 |
| Phe | Ile | Ile | Gly | Leu | Phe | Val | Asn | Ile | Thr | Ala | Leu | Trp | Val | Phe | Ser | |
| | | 35 | | | | | 40 | | | | | 45 | | | | |
| TGT | ACC | ACC | AAG | AAG | AGA | ACC | ACG | GTA | ACC | ATC | TAT | ATG | ATG | AAT | GTG | 370 |
| Cys | Thr | Thr | Lys | Lys | Arg | Thr | Thr | Val | Thr | Ile | Tyr | Met | Met | Asn | Val | |
| | 50 | | | | | 55 | | | | | 60 | | | | | |
| GCA | TTA | GTG | GAC | TTG | ATA | TTT | ATA | ATG | ACT | TTA | CCC | TTT | CGA | ATG | TTT | 418 |
| Ala | Leu | Val | Asp | Leu | Ile | Phe | Ile | Met | Thr | Leu | Pro | Phe | Arg | Met | Phe | |
| 65 | | | | 70 | | | | | 75 | | | | | 80 | | |
| TAT | TAT | GCA | AAA | GAT | GCA | TGG | CCA | TTT | GGA | GAG | TAC | TTC | TGC | CAG | ATT | 466 |
| Tyr | Tyr | Ala | Lys | Asp | Ala | Trp | Pro | Phe | Gly | Glu | Tyr | Phe | Cys | Gln | Ile | |
| | | | 85 | | | | | 90 | | | | | 95 | | | |
| ATT | GGA | GCT | CTC | ACA | GTG | TTT | TAC | CCA | AGC | ATT | GCT | TTA | TGG | CTT | CTT | 514 |
| Ile | Gly | Ala | Leu | Thr | Val | Phe | Tyr | Pro | Ser | Ile | Ala | Leu | Trp | Leu | Leu | |
| | | | 100 | | | | | 105 | | | | | 110 | | | |
| GCC | TTT | ATT | AGT | GCT | GAC | AGA | TAC | ATG | GCC | ATT | GTA | CAG | CCG | AAG | TAC | 562 |
| Ala | Phe | Ile | Ser | Ala | Asp | Arg | Tyr | Met | Ala | Ile | Val | Gln | Pro | Lys | Tyr | |
| | | 115 | | | | | 120 | | | | | 125 | | | | |
| GCC | AAA | GAA | CTT | AAA | AAC | ACG | TGC | AAA | GCC | GTG | CTG | GCG | TGT | GTG | GGA | 610 |
| Ala | Lys | Glu | Leu | Lys | Asn | Thr | Cys | Lys | Ala | Val | Leu | Ala | Cys | Val | Gly | |
| | 130 | | | | | 135 | | | | | 140 | | | | | |
| GTC | TGG | ATA | ATG | ACC | CTG | ACC | ACG | ACC | ACC | CCT | CTG | CTA | CTG | CTC | TAT | 658 |
| Val | Trp | Ile | Met | Thr | Leu | Thr | Thr | Thr | Thr | Pro | Leu | Leu | Leu | Leu | Tyr | |
| 145 | | | | 150 | | | | | 155 | | | | | 160 | | |
| AAA | GAC | CCA | GAT | AAA | GAC | TCC | ACT | CCC | GCC | ACC | TGC | CTC | AAG | ATT | TCT | 706 |
| Lys | Asp | Pro | Asp | Lys | Asp | Ser | Thr | Pro | Ala | Thr | Cys | Leu | Lys | Ile | Ser | |
| | | | 165 | | | | | 170 | | | | | 175 | | | |

FIGURE 2A

```
GAC ATC ATC TAT CTA AAA GCT GTG AAC GTG CTG AAC CTC ACT CGA CTG    754
Asp Ile Ile Tyr Leu Lys Ala Val Asn Val Leu Asn Leu Thr Arg Leu
        180                 185                 190

ACA TTT TTT TTC TTG ATT CCT TTG TTC ATC ATG ATT GGG TGC TAC TTG    802
Thr Phe Phe Phe Leu Ile Pro Leu Phe Ile Met Ile Gly Cys Tyr Leu
        195                 200                 205

GTC ATT ATT CAT AAT CTC CTT CAC GGC AGG ACG TCT AAG CTG AAA CCC    850
Val Ile Ile His Asn Leu Leu His Gly Arg Thr Ser Lys Leu Lys Pro
        210                 215                 220

AAA GTC AAG GAG AAG TCC ATA AGG ATC ATC ATC ACG CTG CTG GTG CAG    898
Lys Val Lys Glu Lys Ser Ile Arg Ile Ile Ile Thr Leu Leu Val Gln
225                 230                 235                 240

GTG CTC GTC TGC TTT ATG CCC TTC CAC ATC TGT TTC GCT TTC CTG ATG    946
Val Leu Val Cys Phe Met Pro Phe His Ile Cys Phe Ala Phe Leu Met
                245                 250                 255

CTG GGA ACG GGG GAG AAC AGT TAC AAT CCC TGG GGA GCC TTT ACC ACC    994
Leu Gly Thr Gly Glu Asn Ser Tyr Asn Pro Trp Gly Ala Phe Thr Thr
        260                 265                 270

TTC CTC ATG AAC CTC AGC ACG TGT CTG GAT GTG ATT CTC TAC TAC ATC    1042
Phe Leu Met Asn Leu Ser Thr Cys Leu Asp Val Ile Leu Tyr Tyr Ile
        275                 280                 285

GTT TCA AAA CAA TTT CAG GCT CGA GTC ATT AGT GTC ATG CTA TAC CGT    1090
Val Ser Lys Gln Phe Gln Ala Arg Val Ile Ser Val Met Leu Tyr Arg
        290                 295                 300

AAT TAC CTT CGA AGC ATG CGC AGA AAA AGT TTC CGA TCT GGT AGT CTA    1138
Asn Tyr Leu Arg Ser Met Arg Arg Lys Ser Phe Arg Ser Gly Ser Leu
305                 310                 315                 320

CGG TCA CTA AGC AAT ATA AAC AGT GAA ATG TTA TGAATAATAA GGTTCTTTCA  1191
Arg Ser Leu Ser Asn Ile Asn Ser Glu Met Leu
                325                 330

TTTCAATCCC ATCAAAATTC ACTTCACTAA CTACTCTGGC GTCAATGGAT ATTCTGTATA  1251

ATACTATCAA GTCCCTTTTC TCTTGAAAAA ATAAATTCAT TATCTTCATT TTAAAAACTT  1311

AAA                                                                1314
```

FIGURE 2B

```
ATTCGGCTTA CTCACTATAG GGCTCGAGCG GCGCCCGGGC AGGTCAAGAC TGCTCCTCTC       60

TGCCGACTAC AACAGATTGG AGCC ATG GCT TTG GAA CAG AAC CAG TCA ACA        111
                           Met Ala Leu Glu Gln Asn Gln Ser Thr
                             1               5

GAT TAT TAT TAT GAG GAA AAT GAA ATG AAC GGC ACT TAT GAC TAC AGT       159
Asp Tyr Tyr Tyr Glu Glu Asn Glu Met Asn Gly Thr Tyr Asp Tyr Ser
 10              15                  20                      25

CAA TAT GAA CTG ATC TGT ATC AAA GAA GAT GTC AGA GAA TTT GCA AAA       207
Gln Tyr Glu Leu Ile Cys Ile Lys Glu Asp Val Arg Glu Phe Ala Lys
                 30                  35                      40

GTT TTC CTC CCT GTA TTC CTC ACA ATA GTT TTC GTC ATT GGA CTT GCA       255
Val Phe Leu Pro Val Phe Leu Thr Ile Val Phe Val Ile Gly Leu Ala
                 45                  50                      55

GGC AAT TCC ATG GTA GTG GCA ATT TAT GCC TAT TAC AAG AAA CAG AGA       303
Gly Asn Ser Met Val Val Ala Ile Tyr Ala Tyr Tyr Lys Lys Gln Arg
             60                  65                  70

ACC AAA ACA GAT GTG TAC ATC CTG AAT TTG GCT GTA GCA GAT TTA CTC       351
Thr Lys Thr Asp Val Tyr Ile Leu Asn Leu Ala Val Ala Asp Leu Leu
         75                  80                  85

CTT CTA TTC ACT CTG CCT TTT TGG GCT GTT AAT GCA GTT CAT GGG TGG       399
Leu Leu Phe Thr Leu Pro Phe Trp Ala Val Asn Ala Val His Gly Trp
 90              95                  100                     105

GTT TTA GGG AAA ATA ATG TGC AAA ATA ACT TCA GCC TTG TAC ACA CTA       447
Val Leu Gly Lys Ile Met Cys Lys Ile Thr Ser Ala Leu Tyr Thr Leu
             110                 115                 120

AAC TTT GTC TCT GGA ATG CAG TTT CTG GCT TGT ATC AGC ATA GAC AGA       495
Asn Phe Val Ser Gly Met Gln Phe Leu Ala Cys Ile Ser Ile Asp Arg
             125                 130                 135

TAT GTG GCA GTA ACT AAA GTC CCC AGC CAA TCA GGA GTG GGA AAA CCA       543
Tyr Val Ala Val Thr Lys Val Pro Ser Gln Ser Gly Val Gly Lys Pro
         140                 145                 150

TGC TGG ATC ATC TGT TCC TGT GTC TGG ATG GCT GCC ATC TTG CTG AGC       591
Cys Trp Ile Ile Cys Ser Cys Val Trp Met Ala Ala Ile Leu Leu Ser
         155                 160                 165
```

FIGURE 3A

| | | | | | | | | | | | | | | | | |
|---|---|---|---|---|---|---|---|---|---|---|---|---|---|---|---|---|
| ATA | CCC | CAG | CTG | GTT | TTT | TAT | ACA | GTA | AAT | GAC | AAT | GCT | AGG | TGC | ATT | 639 |
| Ile | Pro | Gln | Leu | Val | Phe | Tyr | Thr | Val | Asn | Asp | Asn | Ala | Arg | Cys | Ile | |
| 170 | | | | 175 | | | | | 180 | | | | | | 185 | |

| | | | | | | | | | | | | | | | | |
|---|---|---|---|---|---|---|---|---|---|---|---|---|---|---|---|---|
| CCC | ATT | TTC | CCC | CGC | TAC | CTA | AGA | ACA | TCA | ATG | AAA | GCA | TTG | ATT | CAA | 687 |
| Pro | Ile | Phe | Pro | Arg | Tyr | Leu | Arg | Thr | Ser | Met | Lys | Ala | Leu | Ile | Gln | |
| | | | | 190 | | | | | 195 | | | | | 200 | | |

| | | | | | | | | | | | | | | | | |
|---|---|---|---|---|---|---|---|---|---|---|---|---|---|---|---|---|
| ATG | CTA | GAG | ATC | TGC | ATT | GGA | TTT | GTA | GTA | CCC | TTT | CTT | ATT | ATG | GGG | 735 |
| Met | Leu | Glu | Ile | Cys | Ile | Gly | Phe | Val | Val | Pro | Phe | Leu | Ile | Met | Gly | |
| | | | 205 | | | | | 210 | | | | | 215 | | | |

| | | | | | | | | | | | | | | | | |
|---|---|---|---|---|---|---|---|---|---|---|---|---|---|---|---|---|
| GTG | TGC | TAC | TTT | ATC | ACA | GCA | AGG | ACA | CTC | ATG | AAG | ATG | CCA | AAC | ATT | 783 |
| Val | Cys | Tyr | Phe | Ile | Thr | Ala | Arg | Thr | Leu | Met | Lys | Met | Pro | Asn | Ile | |
| | | 220 | | | | | 225 | | | | | 230 | | | | |

| | | | | | | | | | | | | | | | | |
|---|---|---|---|---|---|---|---|---|---|---|---|---|---|---|---|---|
| AAA | ATA | TCT | CGA | CCC | CTA | AAA | GTT | CTG | CTC | ACA | GTC | GTT | ATA | GTT | TTC | 831 |
| Lys | Ile | Ser | Arg | Pro | Leu | Lys | Val | Leu | Leu | Thr | Val | Val | Ile | Val | Phe | |
| 235 | | | | | 240 | | | | | 245 | | | | | | |

| | | | | | | | | | | | | | | | | |
|---|---|---|---|---|---|---|---|---|---|---|---|---|---|---|---|---|
| ATT | GTC | ACT | CAA | CTG | CCT | TAT | AAC | ATT | GTC | AAG | TTC | TGC | CGA | GCC | ATA | 879 |
| Ile | Val | Thr | Gln | Leu | Pro | Tyr | Asn | Ile | Val | Lys | Phe | Cys | Arg | Ala | Ile | |
| 250 | | | | | 255 | | | | | 260 | | | | | 265 | |

| | | | | | | | | | | | | | | | | |
|---|---|---|---|---|---|---|---|---|---|---|---|---|---|---|---|---|
| GAC | ATC | ATC | TAC | TCC | CTG | ATC | ACC | AGC | TGC | AAC | ATG | AGC | AAA | CGC | ATG | 927 |
| Asp | Ile | Ile | Tyr | Ser | Leu | Ile | Thr | Ser | Cys | Asn | Met | Ser | Lys | Arg | Met | |
| | | | | 270 | | | | | 275 | | | | | 280 | | |

| | | | | | | | | | | | | | | | | |
|---|---|---|---|---|---|---|---|---|---|---|---|---|---|---|---|---|
| GAC | ATC | GCC | ATC | CAA | GTC | ACA | GAA | AGC | ATC | GCA | CTC | TTT | CAC | AGC | TGC | 975 |
| Asp | Ile | Ala | Ile | Gln | Val | Thr | Glu | Ser | Ile | Ala | Leu | Phe | His | Ser | Cys | |
| | | | 285 | | | | | 290 | | | | | 295 | | | |

| | | | | | | | | | | | | | | | | |
|---|---|---|---|---|---|---|---|---|---|---|---|---|---|---|---|---|
| CTC | AAC | CCA | ATC | CTT | TAT | GTT | TTT | ATG | GGA | GCA | TCT | TTC | AAA | AAC | TAC | 1023 |
| Leu | Asn | Pro | Ile | Leu | Tyr | Val | Phe | Met | Gly | Ala | Ser | Phe | Lys | Asn | Tyr | |
| | | 300 | | | | | 305 | | | | | 310 | | | | |

| | | | | | | | | | | | | | | | | |
|---|---|---|---|---|---|---|---|---|---|---|---|---|---|---|---|---|
| GTT | ATG | AAA | GTG | GCC | AAG | AAA | TAT | GGG | TCC | TGG | AGA | AGA | CAG | AGA | CAA | 1071 |
| Val | Met | Lys | Val | Ala | Lys | Lys | Tyr | Gly | Ser | Trp | Arg | Arg | Gln | Arg | Gln | |
| 315 | | | | | 320 | | | | | 325 | | | | | | |

| | | | | | | | | | | | | | | | | |
|---|---|---|---|---|---|---|---|---|---|---|---|---|---|---|---|---|
| AGT | GTG | GAG | GAG | TTT | CCT | TTT | GAT | TCT | GAG | GGT | CCT | ACA | GAG | CCA | ACC | 1119 |
| Ser | Val | Glu | Glu | Phe | Pro | Phe | Asp | Ser | Glu | Gly | Pro | Thr | Glu | Pro | Thr | |
| 330 | | | | 335 | | | | | 340 | | | | | 345 | | |

| | | | | | |
|---|---|---|---|---|---|
| AGT | ACT | TTT | AGC | ATT | TAAAGGTAAA ACTGCTCTGC CTTTTGCTTG GATACATATG | 1174 |
| Ser | Thr | Phe | Ser | Ile | |
| | | | | 350 | |

AATGATGCTT TCCCCTCAAA TAAAACATCT GCATTATTCT GAAACTCAAA TCTCAGACGC    1234

CGTGGTTGCA ACTTATAATA AAGAATGGGT TGGGGGAAGG GGGAGAAATA AAAGCCAAGA    1294

AGAAGAAACA AGATAATAAA TGTACAAAAC ATGAAAATTA AAATGAACAA TATAGGAAAA    1354

FIGURE 3B

```
TAATTGTAAC AGGCATAAGT GAATAACACT CTGCTGTAAC GAAGAAAACT TTGTGGTGAT    1414
AATTTTGTAT CTTGGTTGCA GTGGTGCTTA TACCAATCTA CACCAGTGAT AAAATGACCC    1474
AGAACTATTT CCCCCCTTGT TCCCATTTCA ATTTCCTGGT TTTGACATTA TAGTATAATT    1534
ATGTTAGATG GAACC                                                    1549
```

FIGURE 3C

```
GATGCATGCT CGAGCGGCCG CCAGTGTGAT GGATATCTGC AGAATTCGGC TTACTCACTA    60

TAGGGCTCGA GCGGCCGCCC GGGCAGGTCC CTCCAACAAG ACGCAGCACA GAGACACCAC   120

CTACCTAACA CAGGCGACTC TGAGCACTCT CTCTCTGGGA CTGGGCAGAG CGGCAAACGG   180

TCACCTCTCA GACAGCCTTT GACAGACAGG AGGTTCTACA TACCATGGGA GCCAGCCTGC   240

TGTAAGATGG CCACCCTGAG CAATCACAAC CAGCTTGATC TTTCTAATGG CTCACACCCA   300

GAGGAATACA AAATCGCAGC CCTAGTCTTC TACAGCTGCA TCTTCCTGAT TGGGCTGTTT   360

GTTAATGTCA CTGCGTTGTG GGTTTTCAGC TGTACGACCA AGAAAAGAAC ACAGTGACCA   420
```

| | | | | | |
|---|---|---|---|---|---|
| TCTACATG | ATG AAC GTT GCA CTA CTG GAC CTC GTA TTT ATA CTC AGT CTG | | | | 470 |
| | Met Asn Val Ala Leu Leu Asp Leu Val Phe Ile Leu Ser Leu | | | | |
| | 1 | 5 | | 10 | |

```
CCC TTT CGG ATG TTT TAC TAT GCA AAA GGC GAG TGG CCA TTT GGA GAG    518
Pro Phe Arg Met Phe Tyr Tyr Ala Lys Gly Glu Trp Pro Phe Gly Glu
 15              20              25               30

TAC TTC TGC CAC ATT CTT GGG GCC CTG GTG GTG TTT TAC CCA AGC CTC    566
Tyr Phe Cys His Ile Leu Gly Ala Leu Val Val Phe Tyr Pro Ser Leu
             35              40              45

GCT CTG TGG CTT CTT GCT TTC ATT AGT GCT GAC AGA TAC ATG GCC ATC    614
Ala Leu Trp Leu Leu Ala Phe Ile Ser Ala Asp Arg Tyr Met Ala Ile
         50              55              60

GTA CAG CCA AAA TAT GCC AAG GAG CTG AAG AAC ACC GGC AAG GCC GTG    662
Val Gln Pro Lys Tyr Ala Lys Glu Leu Lys Asn Thr Gly Lys Ala Val
             65              70              75

CTT GCG TGT GGG GGG GTC TGG GTA ATG ACC CTG ACC ACC ACT GTC CCC    710
Leu Ala Cys Gly Gly Val Trp Val Met Thr Leu Thr Thr Thr Val Pro
 80              85              90

CTG CTA CTG CTC TAC GAA GAC CCA GAC AAT GCC TCC TCC CCG GCC ACC    758
Leu Leu Leu Leu Tyr Glu Asp Pro Asp Asn Ala Ser Ser Pro Ala Thr
 95              100             105             110

TGC CTG AAG ATC TCC GAC ATC ACC CAC TTA AAA GCT GTC AAC GTG CTC    806
Cys Leu Lys Ile Ser Asp Ile Thr His Leu Lys Ala Val Asn Val Leu
             115             120             125

AAC TTC ACG CGA CTC ATA TTT TTC TTC CTG ATC CCT TTG TTC ATC ATG    854
Asn Phe Thr Arg Leu Ile Phe Phe Phe Leu Ile Pro Leu Phe Ile Met
         130             135             140
```

FIGURE 4A

```
    ATC GGG TGC TAC GTG GTC ATC ATT CAC AGT CTC CTC CGA GGG CAG ACG        902
    Ile Gly Cys Tyr Val Val Ile Ile His Ser Leu Leu Arg Gly Gln Thr
        145                 150                 155

TCT AAG CTG AAG CCC AAG GTC AAG GAG AAG TCC ATA CGG ATC ATC ATG            950
Ser Lys Leu Lys Pro Lys Val Lys Glu Lys Ser Ile Arg Ile Ile Met
    160                 165                 170

ACC CTC CTG CTG CAG GTG CTC GTC TGC TTC GTG CCC TTC CAC ATC TGC            998
Thr Leu Leu Leu Gln Val Leu Val Cys Phe Val Pro Phe His Ile Cys
175                 180                 185                 190

TTT GCC GTC CTG ATG CTA CAA GGA CAG GAG AAC AGC TAT AGC CCC TGG           1046
Phe Ala Val Leu Met Leu Gln Gly Gln Glu Asn Ser Tyr Ser Pro Trp
                195                 200                 205

GGA GCC TTC ACC ACC TTC CTC ATG AAC CTC AGC ACC TGT CTC GAT GTA           1094
Gly Ala Phe Thr Thr Phe Leu Met Asn Leu Ser Thr Cys Leu Asp Val
            210                 215                 220

GTC CTC TAC TAC ATC GTT TCC AAA CAG TTC CAG GCT CGA GTC ATC AGC           1142
Val Leu Tyr Tyr Ile Val Ser Lys Gln Phe Gln Ala Arg Val Ile Ser
        225                 230                 235

GTC ATG CTG TAC CGC AAT TAC CTT CGC AGT GTT CGC AGA AAA AGT GTC           1190
Val Met Leu Tyr Arg Asn Tyr Leu Arg Ser Val Arg Arg Lys Ser Val
    240                 245                 250

CGA TCG GGC AGT TTA CGG TCA CTT AGC AAC ATG AAC AGT GAG ATG CTT           1238
Arg Ser Gly Ser Leu Arg Ser Leu Ser Asn Met Asn Ser Glu Met Leu
255                 260                 265                 270

TGAGTCAGAG CAAGCTGCCA GTCTTCAGTC TCTTT                                    1273
```

FIGURE 4B

```
      G CTA CAA GGA CAG GAG AAC AGC TAT AGC CCC TGG GGA GCC TTC ACC            46
        Leu Gln Gly Gln Glu Asn Ser Tyr Ser Pro Trp Gly Ala Phe Thr
         1               5                  10                  15

ACC TTC CTC ATG AAC CTC AGC ACC TGT CTC GAT GTA GTC CTC TAC TAC          94
      Thr Phe Leu Met Asn Leu Ser Thr Cys Leu Asp Val Val Leu Tyr Tyr
                      20                  25                  30

ATC GTT TCC AAA CAG TTC CAG GCT CGA GTC ATC AGC GTC ATG CTG TAC         142
      Ile Val Ser Lys Gln Phe Gln Ala Arg Val Ile Ser Val Met Leu Tyr
                      35                  40                  45

CGC AAT TAC CTT CGC AGT GTT CGC AGA AAA AGT GTC CGA TCG GGC AGT         190
      Arg Asn Tyr Leu Arg Ser Val Arg Arg Lys Ser Val Arg Ser Gly Ser
                  50                  55                  60

TTA CGG TCA CTT AGC AAC ATG AAC AGT GAG ATG CTT TGAGTCAGAG              236
      Leu Arg Ser Leu Ser Asn Met Asn Ser Glu Met Leu
              65                  70                  75

CAAGCTGCCA GTCTTCAGTC TCTTTAAAAT TCTTTTCCTA TCTACTTTCG GGTGAACCAG       296

CATTCTACAC TATCCAGTCC CTTCTCTAAC AAAGAGAAAT AATAATGATG AACTTTAAAA       356

ACTTCTGCGG TATTCTGTGT ATTCTAGCCA CATGATTAAA AACT                       400
```

FIGURE 5

7 TRANSMEMBRANE RECEPTOR FAMILY MEMBER BLRX

CROSS-REFERENCE TO RELATED APPLICATIONS

This application is a continuation-in-part of U.S. application Ser. No. 09/122,585, filed Jul. 24, 1998 now abandoned, from which priority is claimed pursuant to 35 USC §120, which application is related to U.S. Provisional Application Serial No. 60/053,693, filed Jul. 25, 1997, from which priority is claimed pursuant to 35 USC §119(e)(1), which applications are incorporated herein by reference in their entireties.

FIELD OF THE INVENTION

The present invention relates to compositions related to proteins which function in controlling physiology, development, and/or differentiation of mammalian cells. In particular, it provides proteins which are implicated in the regulation of physiology, development, differentiation, or function of various cell types, e.g., chemokines, 7 transmembrane receptors, reagents related to each, e.g., antibodies or nucleic acids encoding them, and uses thereof.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematoloqy*, Little, Brown and Co., Boston, Mass.; and Paul (ed.) (1993) *Fundamental Immunology* (3d ed.) Raven Press, N.Y.

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which should lead to significant advancements in the diagnosis and therapy of numerous medical abnormalities, e.g., immune system and other disorders.

Lymphokines apparently mediate cellular activities in a variety of ways. They have been shown to support the proliferation, growth, and differentiation of the pluripotential hematopoietic stem cells into vast numbers of progenitors comprising diverse cellular lineages making up a complex immune system. These interactions between the cellular components are necessary for a healthy immune response. These different cellular lineages often respond in a different manner when lymphokines are administered in conjunction with other agents.

The chemokines are a large and diverse superfamily of proteins. The superfamily is subdivided into two classical branches, based upon whether the first two cysteines in the chemokine motif are adjacent (termed the "C—C" branch), or spaced by an intervening residue ("C-X-C"). A more recently identified branch of chemokines lacks two cysteines in the corresponding motif, and is represented by the chemokines known as lymphotactins. Another recently identified branch has three intervening residues between the two cysteines, e.g., CX3C chemokines. See, e.g., Schall and Bacon (1994) *Current Opinion in Immunology* 6:865–873; and Bacon and Schall (1996) *Int. Arch. Allergy & Immunol.* 109:97–109.

The chemokine receptors are typically members of the superfamily of G-protein coupled (or linked) receptors (GPCR, or GPLR). As a class, these receptors are integral membrane proteins characterized by amino acid sequences which contain seven hydrophobic domains. See, e.g., Ruffolo and Hollinger (eds. 1995) *G-Protein Coupled Transmembrane Signaling Mechanisms* CRC Press, Boca Raton, Fla.; Watson and Arkinstall (1994) *The G-Protein Linked Receptor FactsBook* Academic Press, San Diego, Calif.; Peroutka (ed. 1994) *G Protein-Coupled Receptors* CRC Press, Boca Raton, Fla.; Houslay and Milligan (1990) *G-Proteins as Mediators of Cellular Signaling Processes* Wiley and Sons, New York, N.Y.; and Dohlman, et al. (1991) *Ann. Rev. Biochem.* 60:653–688. These hydrophobic domains are predicted to represent transmembrane spanning regions of the proteins. These GPCRs are found in a wide range of organisms and are typically involved in the transmission of signals to the interior of the cell, e.g., through interaction, e.g., with heterotrimeric G-proteins. They respond to a wide and diverse range of agents including lipid analogs, amino acid derivatives, small peptides, and other molecules.

The presumed transmembrane segments are typically 20–25 amino acids in length. Based upon models and data on bacteriorhodopsin, these regions are predicted to be a-helices and be oriented to form a ligand binding pocket. See, e.g., Findley, et al. (1990) *Trends Pharmacol. Sci.* 11:492–499. Other data suggest that the amino termini of the proteins are extracellular, and the carboxy termini are intracellular. See, e.g., Lodish, et al. (1995) *Molecular Cell Biology* 3d ed., Scientific American, New York; and Watson and Arkinstall (1994) *The G-Protein Linked Receptor FactsBook* Academic Press, San Diego, Calif. Phosphorylation cascades have been implicated in the signal transduction pathway of these receptors.

Although the full spectrum of biological activities mediated by these 7 transmembrane receptors has not been fully determined, chemoattractant effects are recognized. Chemokine receptors are notable members of the GPCR family. See, e.g., Samson, et al. (1996) *Biochemistry* 35:3362–3367; and Rapport, et al. (1996) *J. Leukocyte Biology* 59:18–23. The best known biological functions of these chemokine molecules relate to chemoattraction of leukocytes. However, new chemokines and receptors are being discovered, and their biological effects on the various cells responsible for immunological responses are topics of continued study.

Many factors have been identified which influence the differentiation process of precursor cells, or regulate the physiology or migration properties of specific cell types. These observations indicate that other factors exist whose functions in immune function were heretofore unrecognized. These factors provide for biological activities whose spectra of effects may be distinct from known differentiation or activation factors. The absence of knowledge about the structural, biological, and physiological properties of the regulatory factors which regulate cell physiology in vivo prevents the modulation of the effects of such factors.

In addition, other factors exist whose functions in hematopoiesis, neural function, immune development, and leukocyte trafficking were heretofore unrecognized. These receptors mediate biological activities whose spectra of effects are distinct from known differentiation, activation, or other signaling factors. The absence of knowledge about the structural, biological, and physiological properties of the receptors which regulate cell physiology, development, or function prevents the modification of the effects of such factors.

Thus, medical conditions where regulation of the development or physiology of relevant cells is required remain unmanageable.

SUMMARY OF THE INVENTION

The present invention is based, in part, upon the discovery of new genes encoding various chemokines, e.g., those designated CXC N4; or 7 transmembrane receptors, e.g., those designated DNAXCCR10, which encode rodent receptors; and BLRx, which encode primate receptors. Each GPCR gene encodes a polypeptide exhibiting structural and/or sequence homology to 7 transmembrane receptors. Such receptors are typically G-protein coupled (or linked) receptors (GPCR or GPLR), though the complete set of ligands for each has not yet been identified.

The invention also provides mutations (muteins) of the respective natural sequences, fusion proteins, chemical mimetics, antibodies, and other structural or functional analogs. It is also directed to isolated nucleic acids, e.g., genes encoding respective proteins of the invention. Various uses of these different protein, antibody, or nucleic acid compositions are also provided.

The present invention provides a composition selected from the group of: a substantially pure antigenic polypeptide comprising sequence from a CXC N4, a DNAXCCR10, or BLRx; a binding composition comprising an antigen binding portion of an antibody specific for binding to such an antigenic polypeptide; a nucleic acid encoding such an antigenic polypeptide; and a fusion protein comprising at least two non-overlapping segments of at least 10 amino acids of such an antigenic polypeptide.

In certain embodiments of the antigenic polypeptide, it is from a warm blooded animal, e.g., a rodent or primate; it comprises a sequence of FIGS. 1–5; it exhibits a post-translational modification pattern distinct from a natural form of said polypeptide; it is detectably labeled; or it is made by expression of a recombinant nucleic acid. In other embodiments, a sterile form is provided, including, e.g., composition comprising the polypeptide and an acceptable carrier. A detection kit comprising a compartment or container holding such an antigenic polypeptide is also provided.

In other binding composition forms, e.g., antibody embodiments, the polypeptide is a mouse or human protein; the antibody is raised against a peptide sequence of FIGS. 1–5; the antibody is a monoclonal antibody; the binding composition is fused to a heterologous protein, or is detectably labeled. An alternative embodiment is a binding compound comprising an antigen binding fragment of the antibody described. Also provided is a detection kit comprising such a binding compound. With the antibodies are provided methods of purifying a polypeptide using the binding compound or antibody to specifically separate the polypeptides from others, or for detection, e.g., immunohistochemistry or immunoprecipitation.

Nucleic acid embodiments are provided, e.g., where the nucleic acid is in an expression vector and: encodes a polypeptide from a mouse or human; comprises a sequence of a mature protein of FIGS. 1–5; or comprises a deoxyribonucleic acid nucleotide. The invention also provides a kit with such nucleic acids, e.g., which include PCR primers for amplifying such sequences.

With nucleic acids are provided fusion proteins, comprising: a sequence of FIGS. 1–5; and/or sequence of another chemokine or 7 transmembrane receptor, as appropriate. Also provided is a cell comprising a recombinant nucleic acid, as described, and methods of producing a polypeptide comprising expressing the nucleic acid in an expression system.

Other embodiments include methods of modulating physiology or development of a cell, or treating a disorder, with a step of contacting that cell with a composition comprising an agonist or antagonist of the chemokine or receptor. Ordinarily, the cell is a neuron, macrophage, a lymphocyte, or a skin cell, such as found in the epidermis or dermis. Various physiological effects to be modulated include a cellular calcium flux, a chemoattractant response, cellular morphology modification responses, phosphoinositide lipid turnover, an antiviral response, or a proliferative response.

Yet further embodiments are directed to a method comprising administering to a subject in need thereof an effective amount of an agent that modulates the expression or activity of BLRx or fragments thereof. In a further embodiment, the method of treatment or prevention comprises administering to a subject in need thereof an effective amount of an agent that enhances or decreases the activity or expression of BLRx or fragments thereof. The agent can be, for example, a polynucleotide encoding BLRx, a polynucleotide that includes a transcriptional or translational regulator, an antibody that specifically binds to BLRx, an antisense oligonucleotide having a sequence that binds to a sequence encoding BLRx, or a small molecule inhibitor.

The present methods can be directed to the treatment of various disorders, including, for example, wound healing, proliferative disorders, fibrotic disorders, sclerotic disorders, cancer, and angiogenesis.

In another aspect, the present invention encompasses pharmaceutical compositions comprising an effective amount of an agent that modulates the expression or activity of BLRx and a suitable carrier. The agent can be a BLRx agonist or antagonist, for example, or can comprise BLRx and a suitable carrier.

These and other embodiments of the present invention will readily occur to those of ordinary skill in the art in view of the disclosure herein.

BRIEF DESCRIPTION OF THE FIGURES

FIG. 1 (SEQ ID NOS:1 and 2) depicts the partial nucleotide sequence (5' to 3') and corresponding amino acid sequence of a rodent embodiment of a chemokine designated CXC N4 (SEQ ID NO:1). The predicted signal cleavage site is at approximately the gly19-gln20 peptide bond. The CXC motif corresponds to residues cys27 through cys29.

FIGS. 2A–2B (SEQ ID NOS:3 and 4) show the nucleotide sequence (5' to 3') and corresponding amino acid sequence of a human embodiment of a chemokine receptor similar to one designated GPCR W. Nucleotides 1106 and 1139 differ from the previously reported human and canine sequences.

FIGS. 3A–3C (SEQ ID NOS:7 and 8) show the nucleotide sequence (5' to 3') and corresponding amino acid sequence of a human embodiment of a primate 7 transmembrane receptor family member, designated BLRx. Ambiguities in the sequence are as follows: residue 1462 may be G/T; 1473 may be A/C; 1490 may be A/C/G/T; and 1495 may be A/T. Only the first is in the coding sequence, thus residue 193 may be gly or arg.

FIGS. 4A–4B (SEQ ID NOS:9 and 10) show a mouse DNAXCCR10 nucleotide sequence segment and the corresponding amino acid sequence.

FIG. 5 (SEQ ID NOS:5 and 6) shows a partial mouse DNAXCCR10 nucleotide sequence segment and corresponding amino acid sequence.

DETAILED DESCRIPTION OF THE PREFERRED EMBODIMENTS

Figure 6:
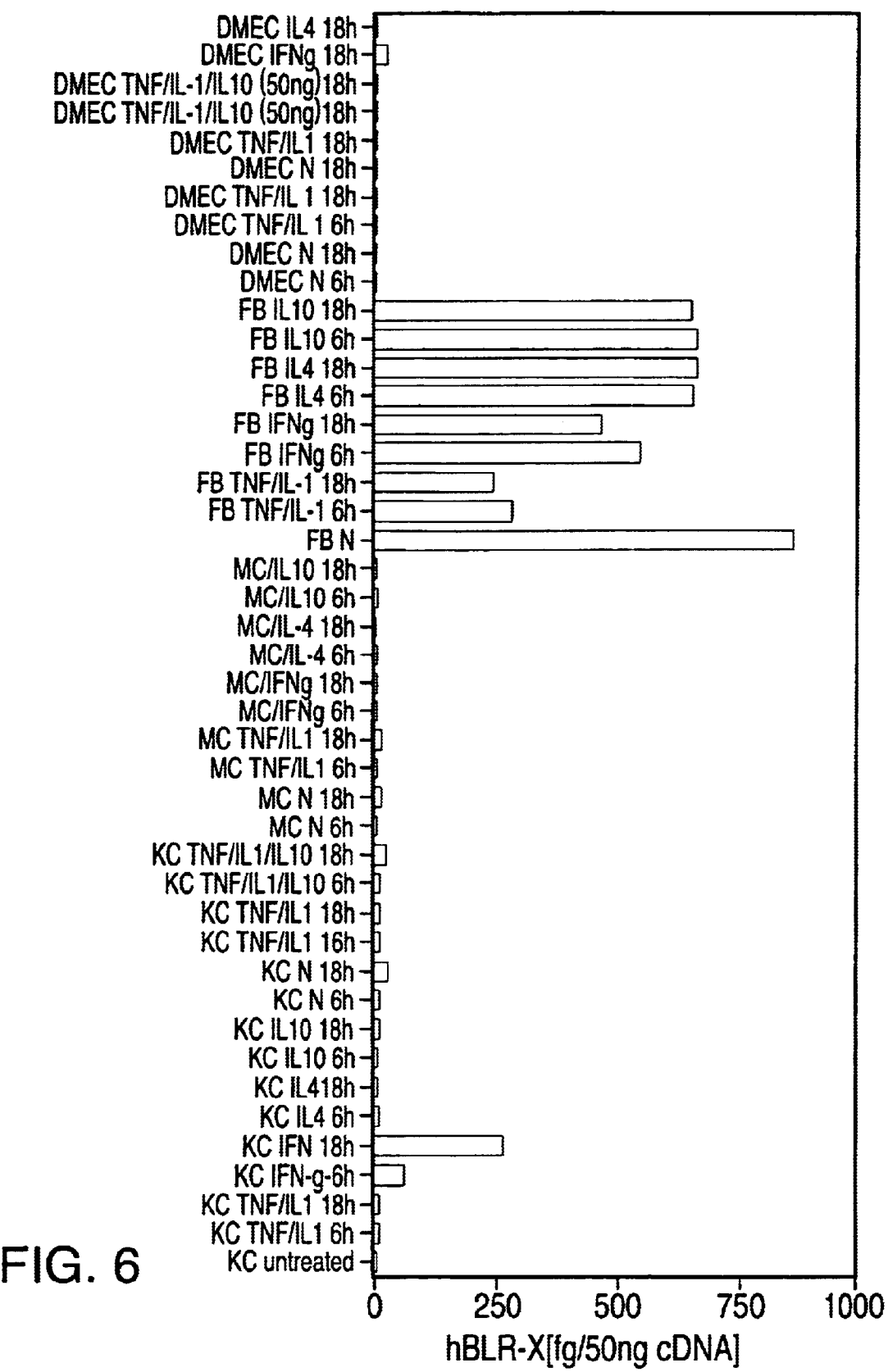
FIG. 6 shows expression levels of BLRx in various tissues and cell types. Expression levels were normalized and expressed as femtograms mRNA per 50 ng total cDNA. Acronyms are as follows: DMEC=dermal microvascular endothelial cell; DMEC N=untreated dermal microvascular endothelial cell; FB=fibroblast; FB N=untreated fibroblast; MC=melanocyte; MC N=untreated melanocyte; and KC=keratinocyte.

All references cited herein are incorporated herein by reference to the same extent as if each individual publication or patent application was specifically and individually indicated to be incorporated by reference.

I. General

The present invention provides DNA sequences encoding various mammalian proteins, including chemokines, or which exhibit structural properties characteristic of a 7 transmembrane receptor. See, e.g., Ruffolo and Hollinger (eds. 1995) *G-Protein Coupled Transmembrane Signaling Mechanisms* CRC Press, Boca Raton, Fla.; Watson and Arkinstall (1994) *The G-Protein Linked Receptor FactsBook* Academic Press, San Diego, Calif.; Peroutka (ed. 1994) *G Protein-Coupled Receptors* CRC Press, Boca Raton, Fla.; Houslay and Milligan (1990) *G-Proteins as Mediators of Cellular Signaling Processes* Wiley and Sons, New York, N.Y. Certain mouse and human embodiments are described herein.

Among the many types of ligands which mediate biology via these receptors are chemokines and certain proteases. Chemokines play an important role in immune and inflammatory responses by inducing migration and adhesion of leukocytes. See, e.g., Schall (1991) *Cytokine* 3:165–183; and Thomson (ed.) *The Cytokine Handbook* Academic Press, NY. Chemokines are secreted by activated leukocytes and act as a chemoattractant for a variety of cells which are involved in inflammation. Besides chemoattractant properties, chemokines have been shown to induce other biological responses, e.g., modulation of second messenger levels such as $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; possible antiviral responses; and others. Thus, the chemokines provided herein may, alone or in combination with other therapeutic reagents, have advantageous combination effects.

Moreover, there are reasons to suggest that chemokines may have effects on other cell types, e.g., attraction or activation of monocytes, dendritic cells, T cells, eosinophils, and/or perhaps on basophils and/or neutrophils. They may also have chemoattractive effects on various neural cells including, e.g., dorsal root ganglia neurons in the peripheral nervous system and/or central nervous system neurons.

G-protein coupled receptors, e.g., chemokine receptors, are important in the signal transduction mechanisms mediated by their ligands. They are useful markers for distinguishing cell populations, and have been implicated as specific receptors for retroviral infections.

The chemokine superfamily was classically divided into two groups exhibiting characteristic structural motifs, the Cys-X-Cys (C-X-C) and Cys—Cys (C—C) families. These were distinguished on the basis of a single amino acid insertion between the NH-proximal pair of cysteine residues and sequence similarity. Typically, the C-X-C chemokines, i.e., IL-8 and MGSA/Gro-α act on neutrophils but not on monocytes, whereas the C—C chemokines, i.e., MIP-1α and RANTES, are potent chemoattractants for monocytes and lymphocytes but not neutrophils. See, e.g., Miller, et al. (1992) *Crit. Rev. Immunol.* 12:17–46. A recently isolated chemokine, lymphotactin, does not belong to either group and may constitute a first member of a third chemokine family, the C family. Lymphotactin does not have a characteristic CC or CXC motif, and acts on lymphocytes but not neutrophils and monocytes. See, e.g., Kelner et al. (1994) *Science* 266:1395–1399. This chemokine defines a new C—C chemokine family. Even more recently, another chemokine exhibiting a CX3C motif has been identified, which establishes a fourth structural class.

The present invention provides additional chemokine reagents, e.g., nucleic acids, proteins and peptides, antibodies, etc., related to the newly discovered chemokine designated rodent CXC N4.

In other embodiments, the invention provides genes encoding novel G-protein coupled receptors, designated mouse DNAXCCR10 and primate BLRx. Their ligands have not yet specifically been identified, but the DNAX-CCR10 responds to binding to the chemokine MIP-3α. See Hieshima, et al. (1997) *J. Biol. Chem.* 272:5846–5853; Hromas, et al. (1997) *Blood* 89:3315–3322; and Baba, et al. (1997) *J. Biol. Chem.* 272:14893–14898. The receptors exhibit structural features typical of known 7 transmembrane spanning receptors, which receptors include chemokine receptors. The receptors may exhibit properties of binding many different cytokines at varying specificities (shared or promiscuous binding specificity) or may exhibit high affinity for one (specific) or a subset (shared) of chemokines. Alternatively, the ligands may be other molecules, including molecules such as epinephrine, serotonin, or glucagon.

The described chemokines or receptors should be important for mediating various aspects of cellular, organ, tissue, or organismal physiology or development.

II. Purified Chemokines; Receptors

Nucleotide and derived amino acid sequences of a novel rodent CXC chemokine, e.g., from mouse, designated CXC N4 are shown in FIG. 1 (SEQ ID NOS:1 and 2). The gene encodes a novel protein exhibiting structure and motifs characteristic of a chemokine. Its closest reported chemokines are the mouse SDF-1, IP-10, and MIG chemokines. See, e.g., Aiuti, et al. (1997) *J. Exp. Med.* 185:111–120; Loetscher, et al. (1996) *J. Exp. Med.* 184:963–969; and Sgadari, et al. (1997) *Blood* 89:2635–2643.

Nucleotide and derived amino acid sequences of a novel primate GPCR, e.g., from human, designated DNAXCCR10, are shown in FIGS. 2A–2B (SEQ ID NOS:3 and 4). Sequence analysis shows closest sequence homology to a human GPCR designated GPCR W (accession number L42324) or to a canine GPCR W (accession number L42326); and to a mouse sequence (accession number AA423677). As indicated above, the receptor responds to binding with chemokine ligand MIP-3α, which immediately allows for screening for ligands since a positive control is available.

Nucleotide and derived amino acid sequences of a rodent GPCR, e.g., from mouse, DNAXCCR10, are shown in FIGS. 4A–4B (SEQ ID NOS:9 and 10). A partial mouse sequence is shown in FIG. 5 (SEQ ID NOS:5 and 6)

Nucleotide and derived amino acid sequences of a novel primate, e.g., from human, 7 transmembrane receptor family member, designated BLRx herein, are shown in FIGS. 3A–3C (SEQ ID NOS:7 and 8). Sequence analysis shows sequence homology to various GPCR family members, particularly the bovine gustative receptor. See Forster, et al. (1996) Cell 13:1037–1047.

Certain general descriptions of physical properties of polypeptides, nucleic acids, and antibodies, where directed to one embodiment clearly are usually applicable to other chemokines or receptors described herein.

These amino acid sequences, provided amino to carboxy, are important in providing sequence information on the chemokine ligand or receptor, allowing for distinguishing the protein from other proteins, particularly naturally occurring versions. Moreover, the sequences allow preparation of peptides to generate antibodies to recognize and distinguish such segments, and allow preparation of oligonucleotide probes, both of which are strategies for isolation, e.g., cloning, of genes encoding such sequences, or related sequences, e.g., natural polymorphic or other variants, including fusion proteins. Similarities of the chemokines have been observed with other cytokines. See, e.g., Bosenberg, et al. (1992) Cell 71:1157–1165; Huang, et. al. (1992) Molecular Biology of the Cell 3:349–362; and Pandiella, et al. (1992) J. Biol. Chem. 267:24028–24033. Likewise for the GPC receptors.

As used herein, the term "CXC N4" shall encompass, when used in a protein context, a protein having an amino acid sequence as shown in FIG. 1. Similarly, by the term "BLRX" is meant a protein with an amino acid sequence as depicted in FIGS. 3A–3C herein. Likewise, the term "DNAXCCR10" refers to a protein having the amino acid sequence depicted in FIGS. 2A–2B. Preferably, such sequences will be the native or natural sequence, e.g., a sequence corresponding to the native sequence from a mammal, such as a primate, rodent, etc. The invention also embraces a polypeptide comprising a significant fragment of such protein. The invention also encompasses a counterpart polypeptide from another mammalian species, e.g., which exhibits similar sequence, and is more homologous in the native coding sequence than other genes from the species. Typically, in the case of homologs of the reference sequence, the molecule will interact with its specific binding components, such as antibodies which bind the sequence, its receptor if the molecule is a chemokine, or the appropriate ligand, if the molecule is a receptor. These binding components, e.g., antibodies, typically bind to the chemokine with high affinity, e.g., at least about 100 nM, usually better than about 30 nM, preferably better than about 10 nM, and more preferably at better than about 3 nM. Similar concepts apply to the binding components which recognize mammalian embodiments for the GPCRs DNAXCCR10 and BLRx.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., about 35, 40, 45, 50, etc. Similar proteins will likely comprise a plurality of such segments. Such fragments may have ends which begin and/or end at virtually all positions, e.g., beginning at residues 1, 2, 3, etc., and ending at, e.g., 54, 53, 52, etc., in all combinatorial pairs in the coding segment. Typically, the plurality will be at least two, more usually at least three, and preferably 5, 7, or even more. While the length minima are provided, longer lengths, of various sizes, may be appropriate, e.g., one of length 7, and two of length 12.

Particularly interesting peptides have ends corresponding to structural domain boundaries, e.g., intracellular or extracellular loops of the receptor embodiments. Such peptides will typically be immunogenic peptides, e.g., including peptides of at least 12, 14, 16, etc., residues or may be concatenated to generate larger polypeptides. Short peptides may be attached or coupled to a larger carrier.

The term "binding composition" refers to molecules that bind with specificity to the respective chemokine or receptor, e.g., in antibody-antigen interaction, or alternatively in a ligand-receptor type fashion. These compositions may be compounds, e.g., proteins, which specifically associate with the chemokine or receptor, including natural physiologically relevant protein—protein interactions, either covalent or non-covalent. The binding composition may be a polymer, or another chemical reagent. No implication as to whether the chemokine presents a concave or convex shape in its ligand-receptor interaction is necessarily represented, other than the interaction exhibit similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of a physiological or natural receptor, see, e.g., Goodman, et al. (eds.) (1990) Goodman & Gilman's: The Pharmacological Bases of Therapeutics (8th ed.), Pergamon Press. The term expressly includes compounds comprising antigen binding portions of antibodies, polyclonal or monoclonal, e.g., which specifically bind to the respective antigen.

Substantially pure means that the protein is free from other contaminating proteins, nucleic acids, and/or other biologicals typically derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. Analyses will typically be by weight, but may be by molar amounts.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state, though in certain circumstances denatured protein will be important. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically at least about 5, preferably at least 6, and typically less than 10, preferably less than 9, and more preferably about 7.5. On some occasions, a detergent will be added, typically a mild non-denaturing one, e.g., CHS (cholesteryl hemisuccinate) or CHAPS (3-([3-cholamido-propyl]dimethylammonio)-1-propane sulfonate), or a low enough concentration as to avoid significant disruption of structural or physiological properties of the protein.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

III. Physical Variants

This invention also encompasses proteins or peptides having substantial amino acid sequence homology with the amino acid sequence of each respective chemokine or chemokine receptor. The variants include species or polymorphic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the appropriate chemokine or receptor, or any percentage between these stated ranges. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and in particularly preferred embodiments, at least 85%, 90%, 95% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

Each of the isolated chemokine or GPC receptor DNAs can be readily modified by nucleotide substitutions, nucleotide deletions, nucleotide insertions, and inversions of nucleotide stretches. These modifications may result in novel DNA sequences which encode these proteins, their derivatives, or proteins having similar physiological, immunogenic, or antigenic activity. These modified sequences can be used to produce mutant proteins or to enhance expression, or to introduce convenient enzyme recognition sites into the nucleotide sequence without significantly affecting the encoded protein sequence. Enhanced expression may involve gene amplification, increased transcription, increased translation, and other mechanisms. Enhanced expression may be useful in the context of wound healing, as described further below. Such mutant receptor derivatives include predetermined or site-specific mutations of the respective protein or its fragments. "Mutant chemokine" or "mutant chemokine receptor" encompasses a polypeptide otherwise falling within the homology definition of the chemokine or receptor as set forth above, but having an amino acid sequence which differs from that of the chemokine or receptor as found in nature, whether by way of deletion, substitution, or insertion. These include amino acid residue substitution levels from none, one, two, three, five, seven, ten, twelve, fifteen . . . 75 etc., and any number within this range. In particular, "site specific mutant" generally includes proteins having significant homology with a protein having sequences of FIGS. 1–5, and as sharing various biological activities, e.g., antigenic or immunogenic, ligand binding, with those sequences, and in preferred embodiments contain a plurality, or most, of disclosed sequences, particularly those found in various related groups of animals. As stated before, it is emphasized that descriptions are generally meant to encompass the various chemokine or receptor proteins from other members of related groups, not limited to the mouse or human embodiments specifically discussed.

Although site specific mutation sites are often predetermined, mutants need not be site specific. Chemokine or receptor mutagenesis can be conducted by making amino acid insertions or deletions, including with PCR mutagenesis. Substitutions, deletions, insertions, or combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements). Many structural features are known about the chemokines and GPCRs which allow determination of whether specific residues are embedded into the core of the secondary or tertiary structures, or whether the residues will have relatively little effect on protein folding. Preferred positions for mutagenesis are those which do not prevent functional folding of the resulting protein.

The mutations in the DNA normally should not place coding sequences out of reading frames and preferably will not create complementary regions that could hybridize to produce secondary mRNA structure such as loops or hairpins. But certain situations exist where such problems are compensated. See, e.g., Gesteland and Atkins (1996) *Ann. Rev. Biochem.* 65:741–768.

The present invention also provides recombinant proteins, e.g., heterologous fusion proteins using segments from these proteins, or antibodies. A heterologous fusion protein is a fusion of proteins or segments which are naturally not normally fused in the same manner. Thus, the fusion product of an immunoglobulin with a receptor polypeptide is a continuous protein molecule having sequences fused in a typical peptide linkage, typically made as a single translation product and exhibiting properties derived from each source peptide. A similar chimeric concept applies to heterologous nucleic acid sequences.

In addition, new constructs may be made from combining similar functional or structural domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of ligand-binding specificities and other functional domains. Such may be chimeric molecules with mixing or matching of the various structural segments, e.g., the β-sheet or α-helix structural domains for the chemokine, or receptor segments corresponding to each of the transmembrane segments (TM1–TM7), or the intracellular (cytosolic, C1–C4) or extracellular (E1–E4) loops from the various receptor types. The C3 loop is particularly important.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to various embodiments of these chemokines or GPCRs may result from the inhibition of binding of the ligand to its receptor, likely through competitive inhibition. Thus, in vitro assays of the present invention will often use isolated protein, membranes from cells expressing a recombinant membrane associated receptor, e.g., ligand binding segments, or fragments attached to solid phase substrates. These assays will also allow for the diagnostic determination of the effects of either binding segment mutations and modifications, or ligand mutations and modifications, e.g., ligand analogs.

This invention also contemplates the use of competitive drug screening assays, e.g., where neutralizing binding compositions, e.g., antibodies, to antigen or receptor fragments compete with a test compound for binding to the protein. In this manner, the antibodies can be used to detect the presence of polypeptides which share one or more antigenic binding sites of the ligand and can also be used to occupy binding sites on the protein that might otherwise interact with a receptor.

Additionally, neutralizing antibodies against a specific chemokine embodiment and soluble fragments of the chemokine which contain a high affinity receptor binding site, can be used to inhibit chemokine activity in tissues, e.g., tissues experiencing abnormal physiology.

"Derivatives" of chemokine proteins include amino acid sequence mutants, glycosylation variants, and covalent or aggregate conjugates with other chemical moieties. Covalent derivatives can be prepared by linkage of functionalities to groups which are found in chemokine amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or nucleoside or nucleotide derivatives, e.g., guanyl derivatized.

A major group of derivatives are covalent conjugates of the respective chemokine or receptor or fragments thereof with other proteins or polypeptides. These derivatives can be synthesized in recombinant culture such as - or C-terminal fusions or by the use of agents known in the art for their usefulness in cross-linking proteins through reactive side groups. Preferred chemokine derivatization sites with cross-linking agents are at free amino groups, carbohydrate moieties, and cysteine residues.

Fusion polypeptides between these chemokines or receptors and other homologous or heterologous proteins, e.g., other chemokines or receptors, are also provided. Many growth factors and cytokines are homodimeric entities, and a repeat construct may have various advantages, including lessened susceptibility to proteolytic cleavage. Moreover, many cytokine receptors require dimerization to transduce a signal, and various dimeric ligands or domain repeats can be desirable. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a ligand, e.g., a receptor-binding segment, so that the presence or location of the fused ligand, or a binding composition, may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, a FLAG fusion, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, guanylation, sulfonation, biotinylation, or the addition or removal of other moieties, particularly those which have molecular shapes similar to phosphate or guanyl groups. In some embodiments, the modifications will be useful labeling reagents, or serve as purification targets, e.g., affinity tags as FLAG.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; and chemical ligation, e.g., Dawson, et al. (1994) *Science* 266:776–779, a method of linking long synthetic peptides by a peptide bond.

This invention also contemplates the use of derivatives of these chemokines or receptors other than variations in amino acid sequence or glycosylation. Such derivatives may involve covalent or aggregative association with chemical moieties. These derivatives generally include: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a chemokine antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-chemokine antibodies or its receptor. These chemokines can also be labeled with a detectable group, for example radioiodinated by the chloramine T procedure, covalently bound to rare earth chelates, or conjugated to a fluorescent moiety for use in diagnostic assays. Purification of chemokine, receptor, or binding compositions may be effected by immobilized antibodies or receptor.

Other modifications may be introduced with the goal of modifying the therapeutic pharmacokinetics or pharmacodynamics of a target chemokine. For example, certain means to minimize the size of the entity may improve its pharmacoaccessibility; other means to maximize size may affect pharmacodynamics. Similarly, changes in ligand binding kinetics or equilibrium of a receptor may be engineered.

A solubilized chemokine or receptor or appropriate fragment of this invention can be used as an immunogen for the production of antisera or antibodies specific for the ligand, receptor, or fragments thereof. The purified proteins can be used to screen monoclonal antibodies or chemokine-binding fragments prepared by immunization with various forms of impure preparations containing the protein. In particular, antibody equivalents include antigen binding fragments of natural antibodies, e.g., Fv, Fab, or F(ab)$_2$. Purified chemokines can also be used as a reagent to detect antibodies generated in response to the presence of elevated levels of the protein or cell fragments containing the protein, both of which may be diagnostic of an abnormal or specific physiological or disease condition. Additionally, chemokine protein fragments, or their concatenates, may also serve as immunogens to produce binding compositions, e.g., antibodies of the present invention, as described immediately below. For example, this invention contemplates antibodies raised against certain amino acid sequences, e.g., in FIGS. 1–5, or proteins containing them. In particular, this invention contemplates antibodies having binding affinity to or being raised against specific fragments, e.g., those which are predicted to lie on the outside surfaces of protein tertiary structure. Similar concepts apply to antibodies specific for receptors of the invention.

The present invention contemplates the isolation of additional closely related species variants. Southern and Northern blot analysis should establish that similar genetic entities exist in other related mammals, and establish the stringency of hybridization conditions to isolate such. It is likely that these chemokines and receptors are widespread in species variants, e.g., among the rodents and the primates.

The invention also provides means to isolate a group of related chemokines or receptors displaying both distinctness and similarities in structure, expression, and function. Elucidation of many of the physiological effects of the proteins will be greatly accelerated by the isolation and characterization of distinct species variants of the ligands. Related genes found, e.g., in various computer databases will also be useful, in many instances, for similar purposes with structurally related proteins. In particular, the present invention provides useful probes or search features for identifying additional homologous genetic entities in different species.

The isolated genes will allow transformation of cells lacking expression of a corresponding chemokine or receptor, e.g., either species types or cells which lack corresponding antigens and exhibit negative background activity. Expression of transformed genes will allow isolation of antigenically pure cell lines, with defined or single specie variants. This approach will allow for more sensitive detection and discrimination of the physiological effects of chemokine or receptor proteins. Subcellular fragments, e.g., cytoplasts or membrane fragments, can be isolated and used.

Dissection of critical structural elements which effect the various differentiation functions provided by ligands is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

In addition, various segments can be substituted between species variants to determine what structural features are important in both receptor binding affinity and specificity, as well as signal transduction. An array of different chemokine or receptor variants will be used to screen for variants exhibiting combined properties of interaction with different species variants.

Intracellular functions would probably involve segments of the receptor which are normally accessible to the cytosol. However, ligand internalization may occur under certain circumstances, and interaction between intracellular components and "extracellular" segments may occur. The specific segments of interaction of a particular chemokine with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of the various chemokines or receptors will be pursued. The controlling elements associated with the proteins may exhibit differential developmental, tissue specific, or other expression patterns. Upstream or downstream genetic regions, e.g., control elements, are of interest. Differential splicing of message may lead to membrane bound forms, soluble forms, and modified versions of ligand.

Structural studies of the proteins will lead to design of new ligands or receptors, particularly analogs exhibiting agonist or antagonist properties on the receptor. This can be combined with previously described screening methods to isolate ligands exhibiting desired spectra of activities.

Expression in other cell types will often result in glycosylation differences in a particular chemokine or receptor. Various species variants may exhibit distinct functions based upon structural differences other than amino acid sequence. Differential modifications may be responsible for differential function, and elucidation of the effects are now made possible.

Thus, the present invention provides important reagents related to a physiological ligand-receptor interaction. Although the foregoing description has focused primarily upon the mouse and human embodiments of the chemokines or receptors specifically described, those of skill in the art will immediately recognize that the invention provides other counterparts, e.g., from related species, rodents or primates.

V. Antibodies

Antibodies can be raised to these chemokines or receptors, including species or polymorphic variants, and fragments thereof, both in their naturally occurring forms and in their recombinant forms. Additionally, antibodies can be raised to chemokines or receptors in either their active or inactive forms, or in their native or denatured forms. Anti-idiotypic antibodies are also contemplated.

Antibodies, including binding fragments and single chain versions, against predetermined fragments of the ligands can be raised by immunization of animals with concatemers or conjugates of the fragments with immunogenic proteins. Monoclonal antibodies are prepared from cells secreting the desired antibody. These antibodies can be screened for binding to normal or defective chemokines or receptors, or screened for agonistic or antagonistic activity. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

The antibodies, including antigen binding fragments, of this invention can have significant preparative, diagnostic, or therapeutic value. They can be useful to purify or label the desired antigen in a sample, or may be potent antagonists that bind to ligand and inhibit binding to receptor or inhibit the ability of a ligand to elicit a biological response. They also can be useful as non-neutralizing antibodies and can be coupled to, or as fusion proteins with, toxins or radionuclides so that when the antibody binds to antigen, a cell expressing it, e.g., on its surface via receptor, is killed. Further, these antibodies can be conjugated to drugs or other therapeutic agents, either directly or indirectly by means of a linker, and may effect drug targeting. Antibodies to receptors may be more easily used to block ligand binding and/or signal transduction.

The antibodies of this invention can also be useful in diagnostic or reagent purification applications. As capture or non-neutralizing antibodies, they can be screened for ability to bind to the chemokines or receptors without inhibiting ligand-receptor binding. As neutralizing antibodies, they can be useful in competitive binding assays. They will also be useful in detecting or quantifying chemokine or receptors, e.g., in immunoassays. They may be used as purification reagents in immunoaffinity columns or as immunohistochemistry reagents.

Ligand or receptor fragments may be concatenated or joined to other materials, particularly polypeptides, as fused or covalently joined polypeptides to be used as immunogens. Short peptides will preferably be made as repeat structures to increase size. A ligand and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin fraction is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256:495–497, which discusses one method of generating monoclonal antibodies. Summarized briefly, this method involves injecting an animal with an immunogen. The animal is then sacrificed and cells taken, e.g., from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance. Large amounts of antibody may be derived from ascites fluid from an animal.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; and Queen et al. (1989) *Proc. Nat'l. Acad. Sci.* 86:10029–10033.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified chemokine protein will be released.

The antibodies may also be used to screen expression libraries for particular expression products. Usually the antibodies used in such a procedure will be labeled with a moiety allowing easy detection of presence of antigen by antibody binding.

Antibodies raised against these chemokines or receptors will also be useful to raise anti-idiotypic antibodies. These will be useful in detecting or diagnosing various immunological conditions related to expression of the respective antigens.

VI. Nucleic Acids

The described peptide sequences and the related reagents are useful in isolating a DNA clone encoding these chemokines or receptors, e.g., from a natural source. Typically, it will be useful in isolating a gene from another individual, and similar procedures will be applied to isolate genes from related species, e.g., rodents or primates. Cross hybridization will allow isolation of ligand from other closely related species. A number of different approaches should be available to successfully isolate a suitable nucleic acid clone. Similar concepts apply to the receptor embodiments.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Alternatively, a chemokine or receptor may be used as a specific binding reagent, and advantage can be taken of its specificity of binding, much like an antibody would be used. The chemokine receptors are typically 7 transmembrane proteins, which could be sensitive to appropriate interaction with lipid or membrane. The signal transduction typically is mediated through a G-protein, through interaction with a G-protein coupled receptor.

For example, the specific binding composition could be used for screening of an expression library made from a cell line which expresses a particular chemokine. The screening can be standard staining of surface expressed ligand, or by panning. Screening of intracellular expression can also be performed by various staining or immunofluorescence procedures. The binding compositions could be used to affinity purify or sort out cells expressing the ligand.

The peptide segments can also be used to predict appropriate oligonucleotides to screen a library, e.g., to isolate species variants. The genetic code can be used to select appropriate oligonucleotides useful as probes for screening. See, e.g., FIGS. 1–5. In combination with polymerase chain reaction (PCR) techniques, synthetic oligonucleotides will be useful in selecting correct clones from a library. Complementary sequences will also be used as probes or primers. Anchored vector or poly-A complementary PCR techniques or complementary DNA of other peptides may be useful. Complementary nucleic acid sequences may also be used as mutagenesis primers.

This invention contemplates use of isolated DNA or fragments to encode a biologically active corresponding chemokine polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact ligand. receptor, or fragment, and have an amino acid sequence as disclosed in FIGS. 1–5. Further, this invention covers the use of isolated or recombinant DNA, or fragments thereof, which encode proteins which are homologous to a chemokine or receptor or which was isolated using such a cDNA encoding a chemokine or receptor as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring purified forms. Thus, for example, products made by transforming cells with any unnaturally occurring vector is encompassed, as are nucleic acids comprising sequence derived using a synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 20 nucleotides, more generally at least about 23 nucleotides, ordinarily at least about 26 nucleotides, more ordinarily at least about 29 nucleotides, often at least about 32 nucleotides, more often at least about 35 nucleotides, typically at least about 38 nucleotides, more typically at least about 41 nucleotides, usually at least about 44 nucleotides, more usually at least about 47 nucleotides, preferably at least about 50 nucleotides, more preferably at least about 53 nucleotides, and in particularly preferred embodiments will be at least about 56 or more nucleotides, e.g., 60, 65, 75, 85, 100, 120, 150, 200, 250, 300, 400, etc. Such fragments may have ends which begin and/or end at virtually all positions, e.g., beginning at nucleotides 1, 2, 3, etc., and ending at, e.g., 300, 299, 298, 287, etc., in combinatorial pairs. Particularly interesting polynucleotides have ends corresponding to structural domain boundaries.

A DNA which codes for a particular chemokine or receptor protein or peptide will be very useful to identify genes, mRNA, and cDNA species which code for related or homologous ligands or receptors, as well as DNAs which code for homologous proteins from different species. There are likely homologs in closely related species, e.g., rodents or primates. Various chemokine proteins should be homologous and are encompassed herein, as would be receptors. However, proteins can readily be isolated under appropriate conditions using these sequences if they are sufficiently homologous. Typically, primate chemokines or receptors are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach* IRL Press, Oxford; and Rosenberg (1992) *J. Clinical Oncology* 10:180–199.

Homologous nucleic acid sequences, when compared, exhibit significant similarity, or identity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from FIGS. 1–5. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. PCR primers will generally have high levels of matches over potentially shorter lengths.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needlman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) *alignments (B) of* 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM, e.g., 20–50 mM. However, the combination of parameters is much more important than the measure of any single parameter. See, e.g., Wetmur and Davidson (1968) *J. Mol. Biol.* 31:349–370. Hybridization under stringent conditions should give a background of at least 2-fold over background, preferably at least 3–5 or more.

Corresponding chemokines or receptors from other closely related species can be cloned and isolated by cross-species hybridization. Alternatively, sequences from a sequence data base may be recognized as having similarity. Homology may be very low between distantly related species, and thus hybridization of relatively closely related species is advisable. Alternatively, preparation of an antibody preparation which exhibits less species specificity may be useful in expression cloning approaches. PCR approaches using segments of conserved sequences will also be used.

VII. Making Chemokines or Receptors; Mimetics

DNA which encodes each respective chemokine, receptor, or fragments thereof can be obtained by chemical synthesis, screening cDNA libraries, or by screening genomic libraries prepared from a wide variety of cell lines or tissue samples. A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence will usually be located 3' to the coding sequence.

This DNA can be expressed in a wide variety of host cells for the synthesis of a full-length ligand or fragments which can in turn, for example, be used to generate polyclonal or monoclonal antibodies; for binding studies; for construction and expression of modified molecules; for expression cloning or purification; and for structure/function studies. Each protein or its fragments can be expressed in host cells that are transformed with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigens or antibodies, or portions thereof, may be expressed as fusions with other proteins.

Expression vectors are typically self-replicating DNA or RNA constructs containing the desired protein gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Thus, the term "control sequences" or "control elements" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Expression vectors also usually contain an origin of replication that allows the vector to replicate independently of the host cell.

The vectors of this invention contain DNA which encode embodiments of a chemokine, receptor, or a fragment thereof, typically encoding a biologically active polypeptide. The DNA can be under the control of a promoter, such as a mammalian or viral promoter and can encode a selection marker. This invention further contemplates use of such expression vectors which are capable of expressing eukaryotic cDNA coding for each chemokine or receptor in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the ligand or its fragments in various hosts using vectors that do not contain a replication origin that is recognized by the host cell. It is also possible to use vectors that cause integration of a chemokine or receptor gene or its fragments into the host DNA by recombination, or to integrate a promoter which controls expression of an endogenous gene. Thus, as used herein, a cell has been "transformed" by exogenous DNA when such exogenous DNA has been introduced inside the cell membrane. Exogenous DNA may or may not be integrated (covalently linked) into chromosomal DNA making up the genome of the cell. A stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

Vectors, as used herein, comprise plasmids, viruses, bacteriophage, integratable DNA fragments, and other vehicles, including those which enable the integration of DNA fragments into the genome of the host. Expression vectors are specialized vectors which contain genetic control elements that effect expression of operably linked genes. Plasmids are the most commonly used form of vector but many other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (1988) (eds.) *Vectors: A Survey of Molecular Cloning Vectors and Their Uses*, Buttersworth, Boston, Mass.

Transformed cells include cells, preferably mammalian, that have been transformed with a chemokine or receptor gene containing vector constructed using recombinant DNA techniques. Transformed host cells usually express the ligand, receptor, or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, from the culture or from the culture medium, or from cell membranes.

For purposes of this invention, DNA sequences are operably linked when they are functionally related to each other. For example, DNA for a presequence or secretory signal is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express these chemokines or their fragments include, but are not limited to, such vectors as those containing the lac promoter (pUC-series); trp promoter (pBR322-trp); lpp promoter (the pIN-series); lambda-pP or pR promoters (pOTS); or hybrid promoters such as ptac (pDR540). See Brosius, et al. (1988) "Expression Vectors Employing Lambda-, trp-, lac-, and lpp-derived Promoters", in Rodriguez and Denhardt (eds.) *Vectors: A Survey of Molecular Cloning Vectors and Their Uses*, Buttersworth, Boston, Chapter 10, pp. 205–236.

Lower eukaryotes, e.g., yeasts and Dictyostelium, may be transformed with chemokine or receptor sequence containing nucleic acids. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active chemokine or receptor proteins. In principle, most any higher eukaryotic tissue culture cell line is workable, e.g., insect baculovirus expression systems, whether from an invertebrate or vertebrate source. However, mammalian cells are preferred, in that the processing, both cotranslationally and posttranslationally, will be typically most like natural. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It will often be desired to express a chemokine or receptor polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, a chemokine or receptor gene may be co-transformed with one or more genes encoding mammalian or other glycosylating enzymes. Using this approach, certain mammalian glycosylation patterns will be achievable or approximated in prokaryote or other cells.

A chemokine, receptor, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that these chemokines and receptors have been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexyl-carbodiimide (DCCD)/additive process can be used. Solid phase and solution phase syntheses are both applicable to the foregoing processes.

These chemokines, receptors, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is typically bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described, e.g., by Merrifield, et al. (1963) in *J. Am. Chem. Soc.* 85:2149–2156.

The prepared ligand and fragments thereof can be isolated and purified from the reaction mixture by means of peptide separation, e.g., by extraction, precipitation, electrophoresis, and various forms of chromatography, and the like. The various chemokines or receptors of this invention can be obtained in varying degrees of purity depending upon its desired use. Purification can be accomplished by use of the protein purification techniques disclosed herein or by the use of the antibodies herein described, e.g., in immunoabsorbant affinity chromatography. This immunoabsorbant affinity chromatography is typically carried out, e.g., by first linking the antibodies to a solid support and then contacting the linked antibodies with solubilized lysates of appropriate source cells, lysates of other cells expressing the ligand or receptor, or lysates or supernatants of cells producing the desired proteins as a result of DNA techniques, see below.

VIII. Uses

The present invention provides reagents which will find use in diagnostic applications as described elsewhere herein, e.g., in the general description for developmental abnormalities, or below in the description of kits for diagnosis.

This invention also provides reagents with significant therapeutic potential. These chemokines and receptors (naturally occurring or recombinant), fragments thereof, and binding compositions, e.g., antibodies thereto, along with compounds identified as having binding affinity to them, should be useful in the treatment of conditions associated with abnormal physiology or development, including inflammatory conditions, e.g., asthma, and epithelial conditions, for example, improper wound healing. In particular, modulation of trafficking of leukocytes is one likely biological activity, but a wider tissue distribution might suggest broader biological activity, including, e.g., antiviral effects. Abnormal proliferation, regeneration, degeneration, and atrophy may be modulated by appropriate therapeutic treatment using the compositions provided herein. For example, a disease or disorder associated with abnormal expression or abnormal signaling by a chemokine or ligand for a receptor should be a likely target for an agonist or antagonist of the ligand.

Various abnormal physiological or developmental conditions are known in cell types shown to possess the chemokine or receptor mRNAs by Northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. Developmental or functional abnormalities, e.g., of the immune system, cause significant medical abnormalities and conditions which may be susceptible to prevention or treatment using compositions provided herein.

Antibodies to the chemokines or receptors, including recombinant forms, can be purified and then used diagnostically or therapeutically, alone or in combination with other chemokines, cytokines, or antagonists thereof. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding. Moreover, modifications to the antibody molecules or antigen binding fragments thereof, may be adopted which affect the pharmacokinetics or pharmacodynamics of the therapeutic entity.

Drug screening using antibodies or receptor or fragments thereof can be performed to identify compounds having binding affinity to each chemokine or receptor, including isolation of associated components. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of a ligand. This invention further contemplates the therapeutic use of antibodies to these chemokines as antagonists, or to the receptors as antagonists or agonists. This approach should be particularly useful with other chemokine or receptor species variants.

Moreover, the novel chemokines and receptors described herein can be used to effect wound healing, as well as to treat a wide variety of disorders associated with proliferative responses. For example, tissue fibrosis is the formation of excessive amounts of fibrotic or scar tissue. Major organs such as the heart, kidney, liver, eye, and skin are prone to chronic scarring. Hypertrophic scars (non-malignant tissue bulk) are a common form of fibrosis caused by burns and other trauma. In addition, there are a number of other fibroproliferative disorders, including scleroderma, keloids, and atherosclerosis, which are associated with general tissue scarring, tumor-like growths in the skin, or sustained scarring of blood vessels. Fibrosis can follow surgery in the form of adhesions, keloid tumors or hypertrophic scarring. Fibrosis causes contractures and joint dislocation following severe burns, wounds or orthopaedic injuries; it can occur in any organ and accompanies many disease states, such as hepatitis (liver cirrhosis), hypertension (heart failure), tuberculosis (pulmonary fibrosis) and diabetes (nephropathy).

Fibrosis, despite the cause, activates a proliferative response related to the events that occur in the healing of skin wounds. Specifically, acute physical damage causes the death of cells, the clotting of blood, an inflammatory response characterized by the migration of inflammatory cells into the lesion, the proliferation of fibroblastic cells in the lesion and the production and deposition of collagen fibers and scars.

As demonstrated herein, BLRx, a representative chemokine receptor, is expressed by fibroblasts, melanocytes and keratinocytes and is involved in wound healing. In particular, enhanced expression of BLRx is associated with the onset of the wound healing process. Thus, the compositions and methods described herein may be used for treating wounds, such as burns and lesions, as well as for treating or preventing any of the various forms of fibrosis described above as the processes involved in fibrosis are the same as those involved in wound healing. Moreover, the compositions and methods may be used in the treatment of hyperproliferative diseases of the epidermis, such as psoriasis and basal cell carcinoma. The methods and compositions are also useful for stimulation of transplanted corneal tissue.

For example, the compositions and methods described herein can be used to enhance wound healing, block the fibrotic process and/or control hyperproliferative disorders using agents that modulate (i.e., either inhibit or enhance) endogenous BLRx production. In treating these disorders, an increase in the concentration of endogenous BLRx may be desired, such as in the case of wound healing. Thus, one method of treatment includes administering a composition that enhances BLRx activity, for example, the ability of BLRx to bind to its ligand, or a composition that enhances endogenous BLRx expression. For example, target cells can be transformed with DNA constructs that either encode BLRx or that include transcriptional and/or translational regulatory elements that enhance expression of endogenous BLRx. The exogenous polynucleotides need not code for exact copies of the endogenous BLRx proteins. Modified protein chains can also be readily designed utilizing various recombinant DNA techniques well known to those skilled in the art and described for instance, in Sambrook et al.,(1989) *Molecular Cloning: A Laboratory Manual* (2d ed.), Vols. 1–3, Cold Spring Harbor Laboratory. For example, hydroxylamine can also be used to introduce single base mutations into the coding region of the gene (Sikorski et al. (1991) *Meth. Enzymol.* 194:302–318). Additionally, an agonist, i.e., a molecule that increases or prolongs the duration of the effect of BLRx, can be administered. Agonists may include proteins, nucleic acids, carbohydrates, or any other molecules that bind to and modulate the effects of the target molecule.

Conversely, a decrease in the concentration or expression of endogenous BLRx may be desired, such as when treating a BLRx-associated proliferative disorder, for example fibrotic or sclerotic disease such as liver sclerosis, lung fibrosis and local/systemic sclerosis, cancer, angiogenesis, and atherosclerosis. In this context, one method of treatment includes the administration of a composition that decreases BLRx activity, or causes a decreased production of endogenous BLRx. Thus, an antagonist, i.e., a molecule which, when bound to BLRx, decreases the extent or duration of the effect of the biological activity, can be administered. Antagonists may include proteins, nucleic acids, carbohydrates, antibodies, or any other molecules which decrease the effect of the target molecule. Thus, one method of treatment includes transforming a target cell with a polynucleotide that includes transcriptional and/or translational regulatory elements that decrease or suppress expression of endogenous BLRx. Another method of treatment includes administering a composition that interferes with the binding of BLRx to its ligand, such as by competitively binding to BLRx or by otherwise decreasing the ability of BLRx to bind to or process its ligand, or by effecting the ability of BLRx to participate in downstream signaling. Thus, in one embodiment of the present invention, methods for treatment of a proliferative disorder involve the administration of a therapeutically effective amount of an antibody which specifically reacts with BLRx. Such antibodies are described in detail above.

In another embodiment, a method of the present invention involves the administration of a therapeutically effective amount of an antisense oligonucleotide having a sequence capable of binding specifically with any sequences of genomic DNA or an mRNA molecule which encodes BLRx, so as to prevent transcripton or translation of BLRx mRNA. By "antisense" is meant a composition containing a nucleic acid sequence which is complementary to the "sense" strand of a specific nucleic acid sequence. Once introduced into a cell, the complementary nucleotides combine with endogenous sequences produced by the cell to form duplexes and to block either transcription or translation. See, e.g., Agrawal, S., ed. (1996) *Antisense Therapeutics*, Humana Press Inc., Totawa N.J.; Alama et al. (1997) *Pharmacol. Res.* 36:171–178; Crooke, S. T. (1997) *Adv. Pharmacol.* 40:1–49; and Lavrosky et al. (1997) *Biochem. Mol. Med.* 62(1):11–22. Antisense sequences can be any nucleic acid material, including DNA, RNA, or any nucleic acid mimics or analogs. See, e.g., Rossi et al. (1991) *Antisense Res. Dev.* 1:285–288; Pardridge et al. (1995) *Proc. Nat. Acad. Sci.* 92:5592–5596; Nielsen and Haaima (1997) *Chem. Soc. Rev.* 96:73–78; and Lee et al. (1998) *Biochemistry* 37:900–1010. Delivery of antisense sequences can be accomplished in a variety of ways, such as through intracellular delivery using a recombinant vector.

Antisense oligonucleotides of about 15 to 25 nucleic acid bases are typically preferred as such are easily synthesized and are capable of producing the desired inhibitory effect. Molecular analogs of antisense oligonucleotides may also be used for this purpose and can have added advantages such as stability, distribution, or limited toxicity advantageous in a pharmaceutical product. In addition, chemically reactive groups, such as iron-linked ethylenediamine-tetraacetic acid (EDTA-Fe), can be attached to antisense oligonucleotides, causing cleavage of the RNA at the site of hybridization. These and other uses of antisense methods to inhibit the in vitro translation of genes are well known in the art. See, e.g., Marcus-Sakura (1988) *Anal. Biochem.* 172:289.

The delivery of polynucleotides, e.g., for delivering BLRx genes or antisense oligonucleotides, can be achieved using recombinant expression vectors, with or without carrier viruses or particles. Such methods are well known in the art. See, e.g., U.S. Pat. Nos. 6,214,804; 6,147,055; 5,703,055; 5,589,466; 5,580,859; Slater et al. (1998) *J. Allergy Clin. Immunol.* 102:469–475. For example, delivery of polynucleotide sequences can be achieved using various viral vectors, including retrovirus and adeno-associated virus vectors. See, e.g., Miller A. D. (1990) *Blood* 76:271; and Uckert and Walther (1994) *Pharmacol. Ther.* 63:323–347. Vectors which can be utilized for antisense gene therapy include, but are not limited to, adenoviruses, herpes viruses, vaccinia, or, preferably, RNA viruses such as retroviruses. Other gene delivery mechanisms that can be used for delivery of polynucleotide sequences to target cells include colloidal dispersion and liposome-derived systems, artificial viral envelopes, and other systems available to one of skill in the art. See, e.g., Rossi, J. J. (1995) *Br. Med. Bull.* 51:217–225; Morris et al. (1997) *Nucl. Acids Res.* 25:2730–2736; and Boado et al. (1998) *J. Pharm. Sci.* 87:1308–1315. For example, delivery systems can make use of macromolecule complexes, nanocapsules, microspheres, beads, and lipid-based systems including oil-in-water emulsions, micelles, mixed micelles, and liposomes.

Site-specific delivery of exogenous genes is also contemplated, such as techniques in which cells are first transfected in culture and stable transfectants are subsequently delivered to the target site. Moreover, delivery can be to the region of the target cell or tissue, i.e., in an area proximal to the tissue to be treated, for example, to the region of the wound.

The quantities of reagents necessary for the various therapies described above will depend upon many different factors, including means of administration, target site, physiological state of the patient, and other medicants administered. Thus, treatment dosages should be titrated to optimize safety and efficacy in various populations, including racial subgroups, age, gender, etc. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Penn. Methods for administration are discussed therein and below, e.g., for oral, intravenous, intraperitoneal, or intramuscular administration, transdermal diffusion, and others. Pharmaceutically acceptable carriers typically include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

A chemokine, fragments thereof, or antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is often preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Carriers may improve storage life, stability, etc. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Penn.; Avis, et al. (eds.) (1993) *Pharmaceutical Dosage Forms: Parenteral Medications* Dekker, New York; Lieberman, et al. (eds.) (1990) *Pharmaceutical Dosage Forms: Tablets* Dekker, New York; and Lieberman, et al. (eds.) (1990) *Pharmaceutical Dosage Forms: Disperse Systems* Dekker, New York. The therapy of this invention may be combined with or used in association with other therapeutic agents. Similar considerations will often apply to receptor based reagents.

Both the naturally occurring and the recombinant forms of the chemokines or receptors of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble chemokine as provided by this invention.

For example, antagonists can normally be found once a ligand has been structurally defined. Testing of potential ligand analogs is now possible upon the development of highly automated assay methods using physiologically responsive cells. In particular, new agonists and antagonists will be discovered by using screening techniques described herein.

Viable cells could also be used to screen for the effects of drugs on respective chemokine or G-protein coupled receptor mediated functions, e.g., second messenger levels, i.e., $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; an antiviral response. and others. Some detection methods allow for elimination of a separation step, e.g., a proximity sensitive detection system. Calcium sensitive dyes will be useful for detecting Ca++levels, with a fluorimeter or a fluorescence cell sorting apparatus.

Rational drug design may also be based upon structural studies of the molecular shapes of the chemokines, other effectors or analogs, or the receptors. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified chemokine or receptor can be coated directly onto plates for use in the aforementioned drug screening techniques, and may be associated with detergents or lipids. However, non-neutralizing antibodies, e.g., to the chemokines or receptors can be used as capture antibodies to immobilize the respective protein on the solid phase.

Similar concepts also apply to the chemokine receptor embodiments of the invention.

IX. Kits

This invention also contemplates use of chemokine or receptor proteins, fragments thereof, peptides, binding compositions, and their fusion products in a variety of diagnostic kits and methods for detecting the presence of ligand, antibodies, or receptors. Typically the kit will have a compartment containing a defined chemokine or receptor peptide or gene segment or a reagent which recognizes one or the other, e.g., binding reagents.

A kit for determining the binding affinity of a test compound to a chemokine or receptor would typically comprise a test compound; a labeled compound, for example an antibody having known binding affinity for the protein; a source of chemokine or receptor (naturally occurring or recombinant); and a means for separating bound from free labeled compound, such as a solid phase for immobilizing the ligand or receptor. Once compounds are screened, those having suitable binding affinity to the ligand or receptor can be evaluated in suitable biological assays, as are well known in the art, to determine whether they act as agonists or antagonists to the receptor. The availability of recombinant chemokine or receptor polypeptides also provide well defined standards for calibrating such assays or as positive control samples.

A preferred kit for determining the concentration of, for example, a chemokine or receptor in a sample would typically comprise a labeled compound, e.g., antibody, having known binding affinity for the target, a source of ligand or receptor (naturally occurring or recombinant) and a means for separating the bound from free labeled compound, for example, a solid phase for immobilizing the chemokine or receptor. Compartments containing reagents, and instructions for use or disposal, will normally be provided.

Antibodies, including antigen binding fragments, specific for the chemokine or receptor, or fragments are useful in diagnostic applications to detect the presence of elevated levels of chemokine, receptor, and/or its fragments. Such diagnostic assays can employ lysates, live cells, fixed cells, immunofluorescence, cell cultures, body fluids, and further can involve the detection of antigens related to the ligand or receptor in serum, or the like. Diagnostic assays may be homogeneous (without a separation step between free reagent and antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the primary antibody to a chemokine or receptor or to a particular fragment thereof. Similar assays have also been extensively discussed in the literature. See, e.g., Harlow and Lane (1988) *Antibodies: A Laboratory Manual*, CSH.

Anti-idiotypic antibodies may have similar uses to diagnose presence of antibodies against a chemokine or receptor, as such may be diagnostic of various abnormal states. For example, overproduction of a chemokine or receptor may result in production of various immunological reactions which may be diagnostic of abnormal physiological states, particularly in various inflammatory or asthma conditions.

Frequently, the reagents for diagnostic assays are supplied in kits, so as to optimize the sensitivity of the assay. For the subject invention, depending upon the nature of the assay, the protocol, and the label, either labeled or unlabeled antibody or labeled chemokine or receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments or containers for each useful reagent. Desirably, the reagents are provided as a dry lyophilized powder, where the reagents may be reconstituted in an aqueous medium providing appropriate concentrations of reagents for performing the assay.

The aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, chemokine, receptor, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating bound from the free ligand, or alternatively bound from free test compound. The chemokine or receptor can be immobilized on various matrixes, perhaps with detergents or associated lipids, followed by washing. Suitable matrixes include plastic such as an ELISA plate, filters, and beads. Methods of immobilizing the chemokine or receptor to a matrix include, without limitation, direct adhesion to plastic, use of a capture antibody, chemical coupling, and biotin-avidin. The last step in this approach may involve the precipitation of antigen/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of the chemokine or receptor. These sequences can be used as probes for detecting levels of the ligand message in samples from patients suspected of having an abnormal condition, e.g., an inflammatory, physiological, or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

X. Receptor for Chemokine; Ligands for Receptors

Having isolated a ligand binding partner of a specific interaction, methods exist for isolating the counter-partner. See, Gearing, et al *EMBO J.* 8:3667–4676 or McMahan, et al. (1991) *EMBO J.* 10:2821–2832. For example, means to label a chemokine without interfering with the binding to its receptor can be determined. For example, an affinity label can be fused to either the amino- or carboxy-terminus of the ligand. An expression library can be screened for specific binding of chemokine, e.g., by cell sorting, or other screening to detect subpopulations which express such a binding component. See, e.g., Ho, et al. (1993) *Proc. Nat'l Acad. Sci.* 90:11267–11271. Alternatively, a panning method may be used. See, e.g., Seed and Aruffo (1987) *Proc. Nat'l. Acad. Sci.* 84:3365–3369.

With a receptor, means to identify the ligand exist. Methods for using the receptor, e.g., on the cell membrane, can be used to screen for ligand by, e.g., assaying for a common G-protein linked signal such as Ca++ flux. See Lerner (1994) *Trends in Neurosciences* 17:142–146. It is likely that the ligands for these receptors are chemokines.

Protein cross-linking techniques with label can be applied to a isolate binding partners of a chemokine. This would allow identification of protein which specifically interacts with a chemokine, e.g., in a ligand-receptor like manner.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1995 and supplements) *Current Protocols in Protein Science* John Wiley and Sons, New York, N.Y.; P. Matsudaira (ed.) (1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, NY; and Crowe, et al. (1992) *QIAexpress: The High Level Expression & Protein Purification System* QUIAGEN, Inc., Chatsworth, Calif.

Standard immunological techniques are described, e.g., in Hertzenberg, et al. (eds. 1996) *Weir's Hanbook of Experimental Immunology* vols 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation and Characterization of Rodent CXC N4 cDNAs

The rodent CXC N4 was identified from a mouse cDNA library. Individual cDNA clones are sequenced using standard methods, e.g., the Taq DyeDeoxy Terminator Cycle Sequencing kit (Applied Biosystems, Foster City, Calif.), and the sequence is further characterized.

The predicted signal sequence corresponds to amino acids met1 to about gly19, so the mature form should begin with gln20 and run about the standard chemokine length, e.g., about 90 to 110 residues. Additional processing may occur in a physiological system.

Computer analysis and alignments for related genes indicates the closest match is to the mouse chemokines SDF-1, IP-10, and MIG. This similarity in sequence may well correlate with similarity in regulation, which suggests related functions. The absence of the ELR motif in the CXC chemokine suggests that it will not bind to the IL-8 receptors, and is probably not angiogenic. It may still be angiostatic, suggesting some possible use in tumor or related therapies. Conversely, an antagonist is likely to block its activity, which suggests therapeutic or research use where angiostasis is undesirable, e.g., wound healing, etc.

Other rodent counterparts should be isolatable using the entire coding portion of this clone as a hybridization probe. A Southern blot or PCR analysis may indicate the extent of homology across species, and either a cDNA library or mRNA can be screened to identify an appropriate cell source. The physiological state of many different cell types may also be evaluated for increased expression of the gene.

III. Isolation and Characterization of GPCR cDNAs

A. Rodent DNAXCCR10

The partial rodent DNAXCCR10 clone was derived from mouse cDNA library. The nucleotide sequence is provided in FIG. 5 (SEQ ID NOS:5 and 6), encoding a polypeptide of about 75 amino acids, at the carboxy terminus of the natural gene.

Computer analysis suggests that the closest related genes are various G-protein coupled receptors. These include the chemokine receptors, and protease, e.g., thrombin, receptors. Structural motifs suggest that the receptor contains motifs characteristic of the chemokine receptor family, and of the protease receptor family. The transmembrane segments, based upon hydrophobicity plots and comparisons with other similar GPCRs, particularly the human and canine GPCR W genes, should be about as follows: TM6 ends at gln2; and TM7 from phe14 to gln36. See, e.g., Loetscher, et al. (1996) *J. Expt'l Med.* 184:963–969. The amino terminal segment is probably an extracellular segment (E1), and the others would be E2 between TM2 and TM3; E3 between TM4 and TM5; and E4 between TM6 and TM7. The intracellular segments should then run I1 between TM1 and TM2; I2 between TM3 and TM4, I3 between TM5 and TM6, and I4 the carboxy terminus from the end of TM7. Additional processing may occur in a physiological system. A computer analysis of GPCR sequences will indicate residues characteristic of the family members.

Other rodent counterparts should be isolatable using the entire coding portion of this mouse clone as a hybridization probe. A Southern blot may indicate the extent of homology across species, and either a cDNA library or mRNA can be screened to identify an appropriate cell source. The physiological state of many different cell types may also be evaluated for increased expression of the gene.

Screening for response to various chemokine ligands indicates that the receptor responds to the presence of the MIP-3α chemokine. See Hieshima, et al. (1997) *J. Biol. Chem.* 272:5846–5853; Hromas, et al. (1997) *Blood* 89:3315–3322; and Baba, et al. (1997) *J. Biol. Chem.* 272:14893–14898. The receptor induced a Ca++ flux upon transfection into various cell types and contacting with the MIP-3α. This receptor is distributed on T cells, as discussed below.

This suggests that the MIP-3α chemokine ligand, or its antagonist, should have activity in recruiting resting T cells and/or NK cells to sites of inflammation. It may also be useful in vaccines, exhibiting certain adjuvant effects. Thus, these reagents may be useful in regulation of inflammation, or initiation of an immune response.

B. Primate BLRx

The primate BLRx clone was derived from a cDNA library made from human sequence, including both olfactory epithelium and tonsil cells.

Computer analysis suggests that the closest related genes are various G-protein coupled receptors. Structural analysis indicates that the receptor contains motifs characteristic of the chemokine receptor family, and exhibits similarity to a bovine gustative receptor. The transmembrane segments, based upon hydrophobicity plots and comparisons with other similar GPCRs, should be about as follows: TM1 from val42 to tyr69; TM2 from val78 to val102; TM3 from ile114 to ile135; TM4 from trp155 to val174; TM5 from ala198 to tyr220; TM6 from lys240 to asn257; TME7 from gln286 to phe305.

Other primate counterparts should be isolatable using the entire coding portion of this human clone as a hybridization probe. A Southern blot may indicate the extent of homology across species, and either a cDNA library or mRNA can be screened to identify an appropriate cell source. The physiological state of many different cell types may also be evaluated for increased expression of the gene.

IV. Preparation of Antibodies

Many standard methods are available for preparation of antibodies. For example, synthetic peptides may be prepared to be used as antigen, administered to an appropriate animal, and either polyclonal or monoclonal antibodies prepared. Short peptides, e.g., less than about 10 amino acids may be expressed as repeated sequences, while longer peptides may be used alone or conjugated to a carrier. For example, with the GPCRs, animals are immunized with peptides or complete proteins from apprpriate portions of FIGS. 1–5. Highest specificity will result when the polypeptides are selected from portions which are most unique, e.g., not from conserved sequence regions. The animals may be used to collect antiserum, or may be used to generate monoclonal antibodies.

Antiserum is evaluated for use, e.g., in an ELISA, and will be evaluated for utility in immunoprecipitation, e.g., typically native, or Western blot, e.g., denatured antigen, analysis. Monoclonal antibodies will also be evaluated for those same uses.

The antibodies provided will be useful as immunoaffinity reagents, as detection reagents, for immunohistochemistry, and as potential therapeutic reagents, either as agonist or antagonist reagents.

V. Assays for Chemotactic Activity of Chemokines

Chemokine proteins are produced, e.g., in COS cells transfected with a plasmid carrying the chemokine cDNA by electroporation. See, Hara, et al. (1992) *EMBO J.* 10:1875–1884. Physical analytical methods may be applied, e.g., CD analysis, to compare tertiary structure to other chemokines to evaluate whether the protein has likely folded into an active conformation. After transfection, a culture supernatant is collected and subjected to bioassays. A mock control, e.g., a plasmid carrying the luciferase cDNA, is used. See, de Wet, et al. (1987) *Mol. Cell. Biol.* 7:725–757. A positive control, e.g., recombinant murine MIP-1α from R&D Systems (Minneapolis, Minn.), is typically used. Likewise, antibodies may be used to block the biological activities, e.g., as a control.

Lymphocyte migration assays are performed as previously described, e.g., in Bacon, et al. (1988) *Br. J. Pharmacol.* 95:966–974. Murine Th2 T cell clones, CDC-25 (see Tony, et al. (1985) *J. Exp. Med.* 161:223–241) and HDK-1 (see Cherwinski, et al. (1987) *J. Exp. Med.* 166:1229–1244), made available from R. Coffman and A. O'Garra (DNAX, Palo Alto, Calif.), respectively, are used as controls.

Ca2+ flux upon chemokine stimulation is measured, e.g., according to the published procedure described in Bacon, et al. (1995) *J. Immunol.* 154:3654–3666.

Maximal numbers of migrating cells in response to the chemokine being tested are measured. See Schall (1993) *J. Exp. Med.* 177:1821–1826. A dose-response curve is determined, preferably giving a characteristic bell shaped dose-response curve.

After stimulation with various chemokines, lymphocytes often exhibit a measurable intracellular Ca2+ flux. MIP-1α, e.g., is capable of inducing immediate transients of calcium mobilization. Typically, the levels of chemokine used in these assays will be comparable to those used for the chemotaxis assays ($1/1000$ dilution of conditioned supernatants).

Retroviral infection assays have also been described, and recent description of certain chemokine receptors in retroviral infection processes may indicate that similar roles may apply these receptors. See, e.g., Balter (1996) *Science* 272:1740 (describing evidence for chemokine receptors as coreceptors for HIV); and Deng, et al. (1996) *Nature* 381:661–666.

For receptors, biological activity may be measured in response to an appropriate ligand. The receptors are transfected into an assortment of cell types, each of which is likely to possess the intracellular signaling components compatible with the expressed receptor. Various ligand sources are tested to find a source of ligand which results in a G-protein coupled response. Alternatively, the cells are tested for Ca++ flux in response to such ligands. Flux may be conveniently measured by electrophysiological means, or by Ca++ sensitive dyes.

VI. Analysis of Individual Variation

From the distribution data, an abundant easily accessible cell type is selected for sampling from individuals. Using PCR techniques, a large population of individuals are analysed for this gene. cDNA or other PCR methods are used to sequence the corresponding gene in the different individuals, and their sequences are compared. This indicates both the extent of divergence among racial or other populations, as well as determining which residues are likely to be modifiable without dramatic effects on function.

VII. Biological Activities, Direct and Indirect

A robust and sensitive assay is selected as described above, e.g., on immune cells, neuronal cells, or stem cells. Chemokine is added to the assay in increasing doses to see if a dose response is detected. For example, in a proliferation assay, cells are plated out in plates. Appropriate culture medium is provided, and chemokine is added to the cells in varying amounts. Growth is monitored over a period of time which will detect either a direct effect on the cells, or an indirect effect of the chemokine.

Alternatively, an activation assay or attraction assay is used. An appropriate cell type is selected, e.g, hematopoietic cells, myeloid (macrophages, neutrophils, polymorphonuclear cells, etc.) or lymphoid (T cell, B cell, or NK cells), neural cells (neurons, neuroglia, oligodendrocytes, astrocytes, etc.), or stem cells, e.g., progenitor cells which differentiate to other cell types, e.g., gut crypt cells and undifferentiated cell types.

Other assays will be those which have been demonstrated with other chemokines. See, e.g., Schall and Bacon (1994) *Current Opinion in Immunology* 6:865–873; and Bacon and Schall (1996) *Int. Arch. Allergy & Immunol.* 109:97–109.

VIII. Structure Activity Relationship

Information on the criticality of particular residues is determined using standard procedures and analysis. Standard mutagenesis analysis is performed, e.g., by generating many different variants at determined positions, e.g., at the structural positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

IX. Chromosomal Localization

The cDNA is labeled, e.g., nick-translated with biotin-14 dATP and hybridized in situ at a final concentration of 5 ng/$\mu$l to metaphases from two normal males. Fluorescence in situ hybridization (FISH) method may be modified from that described by Callen, et al. (1990). *Ann. Genet.* 33:219–221, in that chromosomes are stained before analysis with both prodidium iodide (as counter stain) and DAPI (for chromosome identification). Images of metaphase preparations are captured by a CCD camera and computer enhanced. Identification of the appropriate labeled chromosomes is determined. Localization to the standard locations for such molecule, or different location may also provide information as to function.

X. Expression Analysis of Chemokine/Receptor Genes

RNA blot and hybridization are performed according to the standard methods in Maniatis, et al. (1982) *Molecular Cloning: A Laboratory Manual* Cold Spring Harbor Laboratory Press, Cold Spring Harbor, N.Y. An appropriate fragment or the whole coding sequence of a cDNA fragment is selected for use as a probe. To verify the amount of RNA loaded in each lane, the substrate membrane is reprobed with a control cDNA, e.g., glyceraldehyde 3-phosphate dehydrogenase (G3PDH) cDNA (Clontech, Palo Alto Calif.).

Analysis of mRNA from the appropriate cell source using the probe will determine the natural size of message. It will also indicate whether different sized messages exist. The messages will be subject to analysis after isolation, e.g., by PCR or hybridization techniques.

Northern blot analysis may be performed on many different mRNA sources, e.g., different tissues, different species, or cells exhibiting defined physiological responses, e.g., activation conditions or developmental conditions. However, in certain cases, cDNA libraries may be used to evaluate sources which are difficult to prepare. A "reverse Northern" uses cDNA inserts removed from vector, but multiplicity of bands may reflect either different sized messages, or may be artifact due to incomplete reverse transcription in the preparation of the cDNA library. In such instances, verification may be appropriate by standard Northern analysis.

Similarly, Southern blots may be used to evaluate species distribution of a gene. The stringency of washes of the blot will also provide information as to the extent of homology of various species counterparts.

Tissue distribution, and cell distribution, may be evaluated by immunohistochemistry using antibodies. Alternatively, in situ nucleic acid hybridization may also be used in such analysis. Certain distribution data may be ascertained by the frequency and tissue types where messages have been found and collected in sequence databases, e.g., GenBank or proprietary collections.

A. Rodent CXC N4

The mouse CXC N4 sequence was identified from a mouse sequence data base. There is little distribution data generated at this time.

B. Rodent DNAXCCR10

The rodent DNAXCCR10 was isolated from a mouse cDNA library. A human counterpart nucleic acid is expressed in activate monocytes, and in spleen, lymph node, and appendix, with lesser signals detected in thymus and testis. The signal in testis may be artifact, and should probably be retested under more stringent conditions of isolated tissue. The message appears to be down-regulated in activated PBMC, in activated splenocytes, and activated T cell clones. The message appears to be up-regulated in activated NK cells. It appears up-regulated in activated monocytes, but down-regulated in IL-10 treated monocytes.

The distribution of the receptor points more to the function of the ligand, MIP-3α, as discussed above.

C. Primate BLRx

The BLRx GPCR was identified from primate cDNA library from Weizman Olfactory Epithelium and human tonsilar cells enriched for germinal center B cells. A full length clone was isolated from human spleen, and fragments have been identified in cDNA libraries derived from endometrium stromal cells and synovial fibroblasts.

The message has been detected in cDNA libraries from liver, brain, gall bladder, small intestine, ovary, uterus, spleen, and tonsil. A weak signal was detected in activated monocytes, but this needs to be confirmed. Message has also been detected in various T cell lines and a CHA cell line, but not in the tested Th1, Th2, or Th0 T cell clones. A signal was not detected in PBMC. There appear to be short sequences available from mouse sequences which correspond to a rodent counterpart for this gene.

XI. Biological Activity of BLRx

A. Expression Analysis

In order to identify cells types that express BLRx, a large panel of cDNA libraries was analyzed for the expression of BLRx using quantitative PCR. In particular, cDNA libraries from various cellular sources (indicated in FIG. 6) were prepared as described previously (Bolin, et al. (1997) *J. Neurosci.* 17:5493) and used as templates for Taqman-PCR analyses. Cells were stimulated with various cytokines as indicated in FIG. 6. The cDNAs (50 ng per reaction) were analyzed for the expression of BLRx genes by the Fluorogenic 5'-nuclease PCR assay (Holland, et al. (1991) *Proc. Natl. Acad. Sci. USA* 88:7276), using an ABI Prism 7700 Sequence Detection System (Perkin Elmer, Foster City, Calif.). Reactions were incubated for 2 min at 50° C., denatured for 10 min at 95° C. and subjected to 40 two-step amplification cycles with annealing/extension at 60° C. for 1 min followed by denaturation at 95° C. for 15 sec. The PCR products were analyzed with FAM-labeled probes. Values were expressed as fg/50 ng total cDNA.

Results of the expression analysis are presented in FIG. 6. In particular, expression analysis indicated that BLRx was constitutively expressed in dermal fibroblasts (FB), with expression significantly down-regulated by TNF-α and IL-1β. IFN-γ slightly down-regulated expression by fibroblasts, while IL-4 and IL-10 had no significant effects on expression levels.

BLRx was expressed at lower levels in keratinocytes (KC), melanocytes (MC) and dermal microvascular endothelial cells (DMEC).

These results indicate that BLRx may play a role in wound healing, sclerotic processes, keloid formation, collagen synthesis, scleroderma, systemic sclerosis or in other biological process where these cell types are implicated.

B. In Vivo Wound Healing Studies

In order to test the hypothesis that BLRx is involved in the wound healing process, the following experiment was conducted. Groups of female BALB/c mice (3 animals per group) were anesthetized with an intraperitoneal injection of Ketamine and Zylazine. The dorsal region was shaved and the surgical area disinfected. A 2 cm dorsal incisional wound was made through the epidermis and dermis leaving the subcutaneous muscle layer undisturbed. The wound was closed and the wound and surrounding area covered. Animals were sacrificed at 12 hours, 1, 2, 3, 5, 7 and 10 days following incision.

Figure 7:
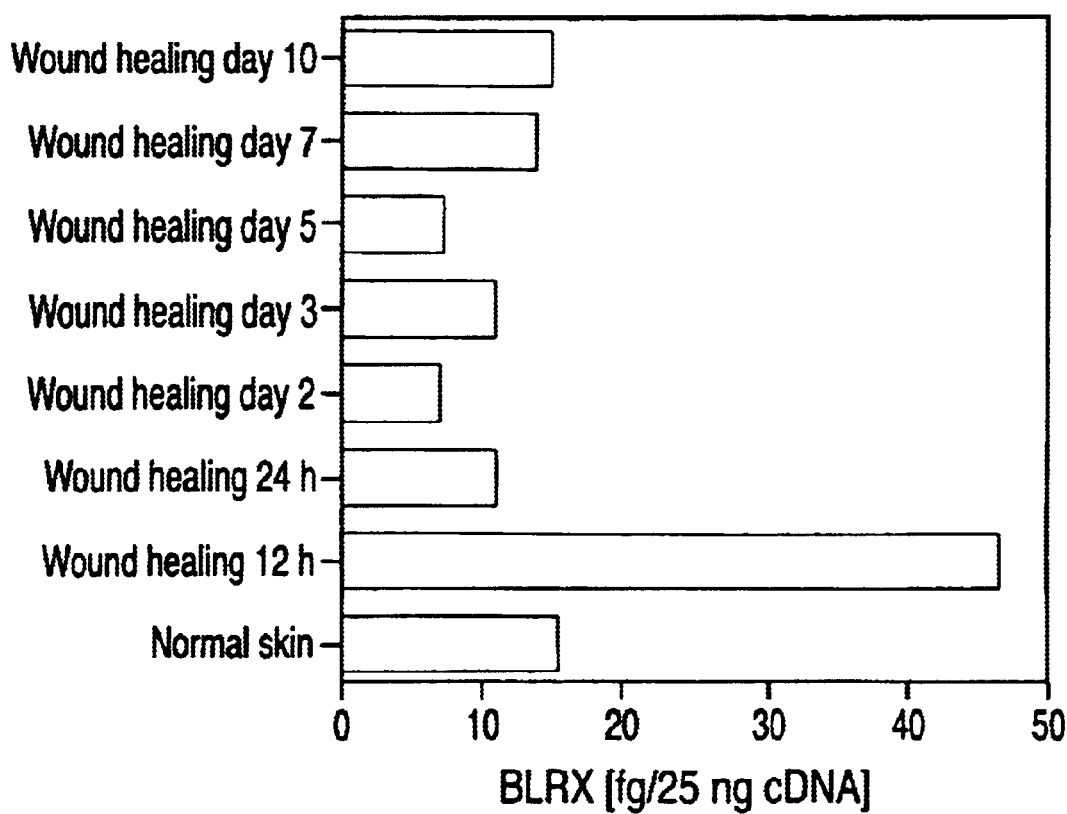
FIG. 7 shows BLRx expression during various phases of wound healing.

Wounds were harvested and RNA was extracted using the RNA STAT 60 method (Tel-Test, New Jersey) and BLRx expression analyzed using Taqman-PCR analysis, as described above. Results are presented in FIG. 7. Values are expressed as fg/25 ng total cDNA. As can be seen, BLRx expression is up-regulated during early wound healing, peaking at 12 hours. The results evidence that BLRx plays a role in wound healing.

XII. Screening for Receptor/Ligand

Labeled reagent is useful for screening of an expression library made from a cell line which expresses a chemokine or receptor, as appropriate. Standard staining techniques are used to detect or sort intracellular or surface expressed ligand, or surface expressing transformed cells are screened by panning. Screening of intracellular expression is performed by various staining or immunofluorescence procedures. See also, e.g., McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at 2–3×10$^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of mMIG-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1M NaN$_3$ for 20 min. Cells are then washed with HBSS/saponin 1×. Add antibody complex to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85–90° C.

Alternatively, the binding compositions are used to affinity purify or sort out cells expressing the ligand or receptor. See, e.g., Sambrook, et al. or Ausubel et al.

Many modification an variations of this invention can be made without departing from its spirit and scope, as will be apparent to those skilled in the art. The specific embodiments described herein are offered by way of example only, and the invention is to be limited only by the terms of the appended claims, along with the full scope of the equivalents to which such claims are entitled.

What is claimed is:

1. An isolated or recombinant nucleic acid encoding a polypeptide comprising the amino acid sequence set forth in SEQ ID NO: 8.

2. An isolated non-human host cell comprising said isolated or recombinant nucleic acid of claim 1.

3. The isolated non-human host cell of claim 2, wherein said isolated non-human host cell is:
   a) a prokaryotic cell;
   b) a eukaryotic cell;
   c) a bacterial cell;
   d) a yeast cell;
   e) an insect cell;
   f) a mammalian cell;
   g) a mouse cell; or
   h) a primate cell.

4. A kit comprising:
   a) a compartment comprising said isolated or recombinant nucleic acid of claim 1;
   b) a compartment further comprising a polypeptide of SEQ ID NO: 8; and/or
   c) instructions for use or disposal of reagents in said kit.

5. The isolated or recombinant nucleic acid of claim 1, wherein the isolated or recombinant nucleic acid comprises the nucleotide sequence set forth in SEQ ID NO: 7.

6. A recombinant vector comprising:
(a) an isolated or recombinant nucleic acid according of claim 1; and
(b) control elements that are operably linked to said isolated or recombinant nucleic acid whereby a coding sequence within said isolated or recombinant nucleic acid can be transcribed and translated in a host cell, and at least one of said control elements is heterologous to said coding sequence.

7. An isolated non-human cell transformed with the recombinant vector of claim 6.

8. A method of producing a recombinant polypeptide comprising:
(a) providing a population of isolated non-human host cells according to claim 7; and
(b) culturing said population of cells under conditions whereby a polypeptide encoded by the coding sequence present in said recombinant vector is expressed.

9. A method of expressing a recombinant polypeptide comprising:
(a) transforming a host cell with the recombinant vector of claim 6; and
(b) causing expression of a polypeptide encoded by the coding sequence present in said recombinant vector.

10. An isolated or recombinant nucleic acid which:
a) hybridizes under wash conditions are at 65° C. and 150 mM salt; and
b) exhibits identity is over at least 75 nucleotides to SEQ ID NO: 7.

11. A kit comprising:
a) a compartment comprising said isolated or recombinant nucleic acid of claim 10;
b) a compartment further comprising a polypeptide of SEQ ID NO: 8; and/or
c) instructions for use or disposal of reagents in said kit.

12. A method for producing a duplex nucleic acid, comprising contacting one strand of the isolated or recombinant nucleic acid of claim 10 to a complementary strand, thereby producing said duplex.

13. An isolated or recombinant nucleic acid encoding a polypeptide consisting of at least 26 contiguous amino acids of the amino acid sequence sat forth in SEQ ID NO: 8.

14. A kit comprising:
a) the isolated or recombinant nucleic acid of claim 13 in a compartment; and
b) instructions for use or disposal of reagents in said kit.

15. An expression vector which comprises the isolated or recombinant nucleic acid of claim 13.

16. An isolated non-human host cell transformed with the expression vector of claim 15.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 18..179

(x) PUBLICATION INFORMATION:
        (H) DOCUMENT NUMBER: US 60/053,693
        (I) FILING DATE: 25-JUL-1997

(xi) SEQUENCE DESCRIPTION: SEQ ID NO: 1:

```
GTTAAACCAC ACTATTC ATG CAA AAG GGT GTA GGG TTA CTG AGG ACA GTT         50
                   Met Gln Lys Gly Val Gly Leu Leu Arg Thr Val
                    1               5                  10

CCC TTG GTA CCT TCA GTC TCT GGT CAG ATT GAC CTT TTG GTA CTG TGT         98
Pro Leu Val Pro Ser Val Ser Gly Gln Ile Asp Leu Leu Val Leu Cys
             15                  20                  25

ATG TGT ATA AAA ACG ACT ACT CCT CAT ATA TTT ATT TCT GAT TAT AAG        146
Met Cys Ile Lys Thr Thr Thr Pro His Ile Phe Ile Ser Asp Tyr Lys
         30                  35                  40

ATA ATA TAT TCT GGA AAA CAC TGG AAA ATA CAT                            179
Ile Ile Tyr Ser Gly Lys His Trp Lys Ile His
         45                  50
```

(2) INFORMATION FOR SEQ ID NO: 2:

(i) SEQUENCE CHARACTERISTICS:
       (A) LENGTH: 54 amino acids
       (B) TYPE: amino acid
       (D) TOPOLOGY: linear (ii) MOLECULE TYPE: protein (xi) SEQUENCE DESCRIPTION: SEQ ID NO: 2:

```
Met Gln Lys Gly Val Gly Leu Leu Arg Thr Val Pro Leu Val Pro Ser
 1               5                  10                  15

Val Ser Gly Gln Ile Asp Leu Leu Val Leu Cys Met Cys Ile Lys Thr
            20                  25                  30

Thr Thr Pro His Ile Phe Ile Ser Asp Tyr Lys Ile Ile Tyr Ser Gly
        35                  40                  45

Lys His Trp Lys Ile His
        50
```

(2) INFORMATION FOR SEQ ID NO: 3:

(i) SEQUENCE CHARACTERISTICS:
       (A) LENGTH: 1314 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 179..1171

(x) PUBLICATION INFORMATION:
       (H) DOCUMENT NUMBER: US 60/053,693
       (I) FILING DATE: 25-JUL-1997

(xi) SEQUENCE DESCRIPTION: SEQ ID NO: 3:

```
GTCTAAAACA AAATACAACA TTTCTTAAAT ACACTGTTTC CAGAAAGAGC TATTTTAACA        60

GAAGCAACTC AAAGATATCC CTTCGACAGA AGTGGAAGTG CTGAAAAATG CTCATCTCT        120

ACACAGACTT TGATGGACA GGAGTTTCTA AGTATCATGC CTACCAACAA GCTGTAAA         178

ATG ATC ACC CTG AAC AAT CAA GAT CAA CCT GTC CCT TTT AAC AGC TCA        226
Met Ile Thr Leu Asn Asn Gln Asp Gln Pro Val Pro Phe Asn Ser Ser
 1               5                  10                  15

CAT CCA GAT GAA TAC AAA ATT GCA GCC CTT GTC TTC TAT AGC TGT ATC        274
His Pro Asp Glu Tyr Lys Ile Ala Ala Leu Val Phe Tyr Ser Cys Ile
            20                  25                  30

TTC ATA ATT GGA TTA TTT GTT AAC ATC ACT GCA TTA TGG GTT TTC AGT        322
Phe Ile Ile Gly Leu Phe Val Asn Ile Thr Ala Leu Trp Val Phe Ser
        35                  40                  45

TGT ACC ACC AAG AAG AGA ACC ACG GTA ACC ATC TAT ATG ATG AAT GTG        370
Cys Thr Thr Lys Lys Arg Thr Thr Val Thr Ile Tyr Met Met Asn Val
    50                  55                  60

GCA TTA GTG GAC TTG ATA TTT ATA ATG ACT TTA CCC TTT CGA ATG TTT        418
Ala Leu Val Asp Leu Ile Phe Ile Met Thr Leu Pro Phe Arg Met Phe
65                  70                  75                  80

TAT TAT GCA AAA GAT GCA TGG CCA TTT GGA GAG TAC TTC TGC CAG ATT        466
Tyr Tyr Ala Lys Asp Ala Trp Pro Phe Gly Glu Tyr Phe Cys Gln Ile
                85                  90                  95

ATT GGA GCT CTC ACA GTG TTT TAC CCA AGC ATT GCT TTA TGG CTT CTT        514
Ile Gly Ala Leu Thr Val Phe Tyr Pro Ser Ile Ala Leu Trp Leu Leu
            100                 105                 110
```

```
GCC TTT ATT AGT GCT GAC AGA TAC ATG GCC ATT GTA CAG CCG AAG TAC        562
Ala Phe Ile Ser Ala Asp Arg Tyr Met Ala Ile Val Gln Pro Lys Tyr
        115                 120                 125

GCC AAA GAA CTT AAA AAC ACG TGC AAA GCC GTG CTG GCG TGT GTG GGA        610
Ala Lys Glu Leu Lys Asn Thr Cys Lys Ala Val Leu Ala Cys Val Gly
130                 135                 140

GTC TGG ATA ATG ACC CTG ACC ACG ACC ACC CCT CTG CTA CTG CTC TAT        658
Val Trp Ile Met Thr Leu Thr Thr Thr Thr Pro Leu Leu Leu Leu Tyr
145                 150                 155                 160

AAA GAC CCA GAT AAA GAC TCC ACT CCC GCC ACC TGC CTC AAG ATT TCT        706
Lys Asp Pro Asp Lys Asp Ser Thr Pro Ala Thr Cys Leu Lys Ile Ser
                165                 170                 175

GAC ATC ATC TAT CTA AAA GCT GTG AAC GTG CTG AAC CTC ACT CGA CTG        754
Asp Ile Ile Tyr Leu Lys Ala Val Asn Val Leu Asn Leu Thr Arg Leu
            180                 185                 190

ACA TTT TTT TTC TTG ATT CCT TTG TTC ATC ATG ATT GGG TGC TAC TTG        802
Thr Phe Phe Phe Leu Ile Pro Leu Phe Ile Met Ile Gly Cys Tyr Leu
        195                 200                 205

GTC ATT ATT CAT AAT CTC CTT CAC GGC AGG ACG TCT AAG CTG AAA CCC        850
Val Ile Ile His Asn Leu Leu His Gly Arg Thr Ser Lys Leu Lys Pro
    210                 215                 220

AAA GTC AAG GAG AAG TCC ATA AGG ATC ATC ATC ACG CTG CTG GTG CAG        898
Lys Val Lys Glu Lys Ser Ile Arg Ile Ile Ile Thr Leu Leu Val Gln
225                 230                 235                 240

GTG CTC GTC TGC TTT ATG CCC TTC CAC ATC TGT TTC GCT TTC CTG ATG        946
Val Leu Val Cys Phe Met Pro Phe His Ile Cys Phe Ala Phe Leu Met
                245                 250                 255

CTG GGA ACG GGG GAG AAC AGT TAC AAT CCC TGG GGA GCC TTT ACC ACC        994
Leu Gly Thr Gly Glu Asn Ser Tyr Asn Pro Trp Gly Ala Phe Thr Thr
            260                 265                 270

TTC CTC ATG AAC CTC AGC ACG TGT CTG GAT GTG ATT CTC TAC TAC ATC       1042
Phe Leu Met Asn Leu Ser Thr Cys Leu Asp Val Ile Leu Tyr Tyr Ile
        275                 280                 285

GTT TCA AAA CAA TTT CAG GCT CGA GTC ATT AGT GTC ATG CTA TAC CGT       1090
Val Ser Lys Gln Phe Gln Ala Arg Val Ile Ser Val Met Leu Tyr Arg
    290                 295                 300

AAT TAC CTT CGA AGC ATG CGC AGA AAA AGT TTC CGA TCT GGT AGT CTA       1138
Asn Tyr Leu Arg Ser Met Arg Arg Lys Ser Phe Arg Ser Gly Ser Leu
305                 310                 315                 320

CGG TCA CTA AGC AAT ATA AAC AGT GAA ATG TTA TGAATAATAA GGTTCTTT       1191
Arg Ser Leu Ser Asn Ile Asn Ser Glu Met Leu
                325                 330

TTTCAATCCC ATCAAAATTC ACTTCACTAA CTACTCTGGC GTCAATGGAT ATTCTGTA       1251

ATACTATCAA GTCCCTTTTC TCTTGAAAAA ATAAATTCAT TATCTTCATT TTAAAAAC       1311

AAA                                                                    1314

(2) INFORMATION FOR SEQ ID NO: 4:

(i) SEQUENCE CHARACTERISTICS:
        (A) LENGTH: 331 amino acids
        (B) TYPE: amino acid
        (D) TOPOLOGY: linear (ii) MOLECULE TYPE: protein (xi) SEQUENCE DESCRIPTION: SEQ ID NO: 4:

Met Ile Thr Leu Asn Asn Gln Asp Gln Pro Val Pro Phe Asn Ser Ser
 1               5                  10                  15

His Pro Asp Glu Tyr Lys Ile Ala Ala Leu Val Phe Tyr Ser Cys Ile
            20                  25                  30
```

```
Phe Ile Ile Gly Leu Phe Val Asn Ile Thr Ala Leu Trp Val Phe Ser
         35                  40                  45

Cys Thr Thr Lys Lys Arg Thr Thr Val Thr Ile Tyr Met Met Asn Val
 50                  55                  60

Ala Leu Val Asp Leu Ile Phe Ile Met Thr Leu Pro Phe Arg Met Phe
 65                  70                  75                  80

Tyr Tyr Ala Lys Asp Ala Trp Pro Phe Gly Glu Tyr Phe Cys Gln Ile
                 85                  90                  95

Ile Gly Ala Leu Thr Val Phe Tyr Pro Ser Ile Ala Leu Trp Leu Leu
             100                 105                 110

Ala Phe Ile Ser Ala Asp Arg Tyr Met Ala Ile Val Gln Pro Lys Tyr
         115                 120                 125

Ala Lys Glu Leu Lys Asn Thr Cys Lys Ala Val Leu Ala Cys Val Gly
 130                 135                 140

Val Trp Ile Met Thr Leu Thr Thr Thr Pro Leu Leu Leu Leu Tyr
145                 150                 155                 160

Lys Asp Pro Asp Lys Asp Ser Thr Pro Ala Thr Cys Leu Lys Ile Ser
                 165                 170                 175

Asp Ile Ile Tyr Leu Lys Ala Val Asn Val Leu Asn Leu Thr Arg Leu
             180                 185                 190

Thr Phe Phe Phe Leu Ile Pro Leu Phe Ile Met Ile Gly Cys Tyr Leu
         195                 200                 205

Val Ile Ile His Asn Leu Leu His Gly Arg Thr Ser Lys Leu Lys Pro
 210                 215                 220

Lys Val Lys Glu Lys Ser Ile Arg Ile Ile Thr Leu Leu Val Gln
225                 230                 235                 240

Val Leu Val Cys Phe Met Pro Phe His Ile Cys Phe Ala Phe Leu Met
                 245                 250                 255

Leu Gly Thr Gly Glu Asn Ser Tyr Asn Pro Trp Gly Ala Phe Thr Thr
             260                 265                 270

Phe Leu Met Asn Leu Ser Thr Cys Leu Asp Val Ile Leu Tyr Tyr Ile
         275                 280                 285

Val Ser Lys Gln Phe Gln Ala Arg Val Ile Ser Val Met Leu Tyr Arg
 290                 295                 300

Asn Tyr Leu Arg Ser Met Arg Arg Lys Ser Phe Arg Ser Gly Ser Leu
305                 310                 315                 320

Arg Ser Leu Ser Asn Ile Asn Ser Glu Met Leu
                 325                 330

(2) INFORMATION FOR SEQ ID NO: 5:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..226

(x) PUBLICATION INFORMATION:
        (H) DOCUMENT NUMBER: US 60/053,693
        (I) FILING DATE: 25-JUL-1997

(xi) SEQUENCE DESCRIPTION: SEQ ID NO: 5:
```

```
G CTA CAA GGA CAG GAG AAC AGC TAT AGC CCC TGG GGA GCC TTC ACC          46
  Leu Gln Gly Gln Glu Asn Ser Tyr Ser Pro Trp Gly Ala Phe Thr
   1               5                  10                 15

ACC TTC CTC ATG AAC CTC AGC ACC TGT CTC GAT GTA GTC CTC TAC TAC         94
Thr Phe Leu Met Asn Leu Ser Thr Cys Leu Asp Val Val Leu Tyr Tyr
            20                  25                  30

ATC GTT TCC AAA CAG TTC CAG GCT CGA GTC ATC AGC GTC ATG CTG TAC        142
Ile Val Ser Lys Gln Phe Gln Ala Arg Val Ile Ser Val Met Leu Tyr
        35                  40                  45

CGC AAT TAC CTT CGC AGT GTT CGC AGA AAA AGT GTC CGA TCG GGC AGT        190
Arg Asn Tyr Leu Arg Ser Val Arg Arg Lys Ser Val Arg Ser Gly Ser
            50                  55                  60

TTA CGG TCA CTT AGC AAC ATG AAC AGT GAG ATG CTT TGAGTCAGAG             236
Leu Arg Ser Leu Ser Asn Met Asn Ser Glu Met Leu
        65                  70                  75

CAAGCTGCCA GTCTTCAGTC TCTTTAAAAT TCTTTTCCTA TCTACTTTCG GGTGAACCA       296

CATTCTACAC TATCCAGTCC CTTCTCTAAC AAAGAGAAAT AATAATGATG AACTTTAAA       356

ACTTCTGCGG TATTCTGTGT ATTCTAGCCA CATGATTAAA AACT                       400

(2) INFORMATION FOR SEQ ID NO: 6:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO: 6:

Leu Gln Gly Gln Glu Asn Ser Tyr Ser Pro Trp Gly Ala Phe Thr Thr
 1               5                  10                  15

Phe Leu Met Asn Leu Ser Thr Cys Leu Asp Val Val Leu Tyr Tyr Ile
            20                  25                  30

Val Ser Lys Gln Phe Gln Ala Arg Val Ile Ser Val Met Leu Tyr Arg
        35                  40                  45

Asn Tyr Leu Arg Ser Val Arg Arg Lys Ser Val Arg Ser Gly Ser Leu
        50                  55                  60

Arg Ser Leu Ser Asn Met Asn Ser Glu Met Leu
65                  70                  75

(2) INFORMATION FOR SEQ ID NO: 7:

(i) SEQUENCE CHARACTERISTICS:
        (A) LENGTH: 1549 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 85..1134

(ix) FEATURE:
        (A) NAME/KEY: misc_feature
        (B) LOCATION: 661
        (D) OTHER INFORMATION: /note= "residue 661 may be G or C;
             actually found to be A"

(ix) FEATURE:
        (A) NAME/KEY: misc_feature
        (B) LOCATION: 1462
        (D) OTHER INFORMATION: /note= ""residue 1462 may be G or
             T""
```

-continued

```
      (ix) FEATURE:
            (A) NAME/KEY: misc_feature
            (B) LOCATION: 1473
            (D) OTHER INFORMATION: /note= """residue 1473 may be A or
                C"""

(ix) FEATURE:
            (A) NAME/KEY: misc_feature
            (B) LOCATION: 1490
            (D) OTHER INFORMATION: /note= """residue 1490 may be A, C,
                T, or G"""

(ix) FEATURE:
            (A) NAME/KEY: misc_feature
            (B) LOCATION: 1495
            (D) OTHER INFORMATION: /note= """residue 1495 may be A or
                T"""

(x) PUBLICATION INFORMATION:
            (H) DOCUMENT NUMBER: US 60/053,693
            (I) FILING DATE: 25-JUL-1997

(xi) SEQUENCE DESCRIPTION: SEQ ID NO: 7:

ATTCGGCTTA CTCACTATAG GGCTCGAGCG GCGCCCGGGC AGGTCAAGAC TGCTCCTCTC     60

TGCCGACTAC AACAGATTGG AGCC ATG GCT TTG GAA CAG AAC CAG TCA ACA       111
                          Met Ala Leu Glu Gln Asn Gln Ser Thr
                            1               5

GAT TAT TAT TAT GAG GAA AAT GAA ATG AAC GGC ACT TAT GAC TAC AGT      159
Asp Tyr Tyr Tyr Glu Glu Asn Glu Met Asn Gly Thr Tyr Asp Tyr Ser
 10              15                  20                  25

CAA TAT GAA CTG ATC TGT ATC AAA GAA GAT GTC AGA GAA TTT GCA AAA      207
Gln Tyr Glu Leu Ile Cys Ile Lys Glu Asp Val Arg Glu Phe Ala Lys
             30                  35                  40

GTT TTC CTC CCT GTA TTC CTC ACA ATA GTT TTC GTC ATT GGA CTT GCA      255
Val Phe Leu Pro Val Phe Leu Thr Ile Val Phe Val Ile Gly Leu Ala
                 45                  50                  55

GGC AAT TCC ATG GTA GTG GCA ATT TAT GCC TAT TAC AAG AAA CAG AGA      303
Gly Asn Ser Met Val Val Ala Ile Tyr Ala Tyr Tyr Lys Lys Gln Arg
             60                  65                  70

ACC AAA ACA GAT GTG TAC ATC CTG AAT TTG GCT GTA GCA GAT TTA CTC      351
Thr Lys Thr Asp Val Tyr Ile Leu Asn Leu Ala Val Ala Asp Leu Leu
     75                  80                  85

CTT CTA TTC ACT CTG CCT TTT TGG GCT GTT AAT GCA GTT CAT GGG TGG      399
Leu Leu Phe Thr Leu Pro Phe Trp Ala Val Asn Ala Val His Gly Trp
 90                  95                 100                 105

GTT TTA GGG AAA ATA ATG TGC AAA ATA ACT TCA GCC TTG TAC ACA CTA      447
Val Leu Gly Lys Ile Met Cys Lys Ile Thr Ser Ala Leu Tyr Thr Leu
                110                 115                 120

AAC TTT GTC TCT GGA ATG CAG TTT CTG GCT TGT ATC AGC ATA GAC AGA      495
Asn Phe Val Ser Gly Met Gln Phe Leu Ala Cys Ile Ser Ile Asp Arg
             125                 130                 135

TAT GTG GCA GTA ACT AAA GTC CCC AGC CAA TCA GGA GTG GGA AAA CCA      543
Tyr Val Ala Val Thr Lys Val Pro Ser Gln Ser Gly Val Gly Lys Pro
         140                 145                 150

TGC TGG ATC ATC TGT TCC TGT GTC TGG ATG GCT GCC ATC TTG CTG AGC      591
Cys Trp Ile Ile Cys Ser Cys Val Trp Met Ala Ala Ile Leu Leu Ser
155                 160                 165

ATA CCC CAG CTG GTT TTT TAT ACA GTA AAT GAC AAT GCT AGG TGC ATT      639
Ile Pro Gln Leu Val Phe Tyr Thr Val Asn Asp Asn Ala Arg Cys Ile
170                 175                 180                 185

CCC ATT TTC CCC CGC TAC CTA AGA ACA TCA ATG AAA GCA TTG ATT CAA      687
Pro Ile Phe Pro Arg Tyr Leu Arg Thr Ser Met Lys Ala Leu Ile Gln
                190                 195                 200
```

```
ATG CTA GAG ATC TGC ATT GGA TTT GTA GTA CCC TTT CTT ATT ATG GGG      735
Met Leu Glu Ile Cys Ile Gly Phe Val Val Pro Phe Leu Ile Met Gly
        205                 210                 215

GTG TGC TAC TTT ATC ACA GCA AGG ACA CTC ATG AAG ATG CCA AAC ATT      783
Val Cys Tyr Phe Ile Thr Ala Arg Thr Leu Met Lys Met Pro Asn Ile
            220                 225                 230

AAA ATA TCT CGA CCC CTA AAA GTT CTG CTC ACA GTC GTT ATA GTT TTC      831
Lys Ile Ser Arg Pro Leu Lys Val Leu Leu Thr Val Val Ile Val Phe
    235                 240                 245

ATT GTC ACT CAA CTG CCT TAT AAC ATT GTC AAG TTC TGC CGA GCC ATA      879
Ile Val Thr Gln Leu Pro Tyr Asn Ile Val Lys Phe Cys Arg Ala Ile
250                 255                 260                 265

GAC ATC ATC TAC TCC CTG ATC ACC AGC TGC AAC ATG AGC AAA CGC ATG      927
Asp Ile Ile Tyr Ser Leu Ile Thr Ser Cys Asn Met Ser Lys Arg Met
                270                 275                 280

GAC ATC GCC ATC CAA GTC ACA GAA AGC ATC GCA CTC TTT CAC AGC TGC      975
Asp Ile Ala Ile Gln Val Thr Glu Ser Ile Ala Leu Phe His Ser Cys
            285                 290                 295

CTC AAC CCA ATC CTT TAT GTT TTT ATG GGA GCA TCT TTC AAA AAC TAC     1023
Leu Asn Pro Ile Leu Tyr Val Phe Met Gly Ala Ser Phe Lys Asn Tyr
        300                 305                 310

GTT ATG AAA GTG GCC AAG AAA TAT GGG TCC TGG AGA AGA CAG AGA CAA     1071
Val Met Lys Val Ala Lys Lys Tyr Gly Ser Trp Arg Arg Gln Arg Gln
    315                 320                 325

AGT GTG GAG GAG TTT CCT TTT GAT TCT GAG GGT CCT ACA GAG CCA ACC     1119
Ser Val Glu Glu Phe Pro Phe Asp Ser Glu Gly Pro Thr Glu Pro Thr
330                 335                 340                 345

AGT ACT TTT AGC ATT TAAAGGTAAA ACTGCTCTGC CTTTTGCTTG GATACATATG     1174
Ser Thr Phe Ser Ile
                350

AATGATGCTT TCCCCTCAAA TAAAACATCT GCATTATTCT GAAACTCAAA TCTCAGAC     1234

CGTGGTTGCA ACTTATAATA AAGAATGGGT TGGGGGAAGG GGGAGAAATA AAAGCCAA     1294

AGAAGAAACA AGATAATAAA TGTACAAAAC ATGAAAATTA AAATGAACAA TATAGGAA     1354

TAATTGTAAC AGGCATAAGT GAATAACACT CTGCTGTAAC GAAGAAAACT TTGTGGTG     1414

AATTTTGTAT CTTGGTTGCA GTGGTGCTTA TACCAATCTA CACCAGTGAT AAAATGAC     1474

AGAACTATTT CCCCCCTTGT TCCCATTTCA ATTTCCTGGT TTTGACATTA TAGTATAA     1534

ATGTTAGATG GAACC                                                    1549
```

(2) INFORMATION FOR SEQ ID NO: 8:

(i) SEQUENCE CHARACTERISTICS:
        (A) LENGTH: 350 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ala Leu Glu Gln Asn Gln Ser Thr Asp Tyr Tyr Glu Glu Asn
 1               5                  10                  15

Glu Met Asn Gly Thr Tyr Asp Tyr Ser Gln Tyr Glu Leu Ile Cys Ile
                20                  25                  30

Lys Glu Asp Val Arg Glu Phe Ala Lys Val Phe Leu Pro Val Phe Leu
            35                  40                  45

Thr Ile Val Phe Val Ile Gly Leu Ala Gly Asn Ser Met Val Val Ala
        50                  55                  60

Ile Tyr Ala Tyr Tyr Lys Lys Gln Arg Thr Lys Thr Asp Val Tyr Ile
```

```
            65                  70                  75                  80
Leu Asn Leu Ala Val Ala Asp Leu Leu Leu Phe Thr Leu Pro Phe
                    85                  90                  95

Trp Ala Val Asn Ala Val His Gly Trp Val Leu Gly Lys Ile Met Cys
                100                 105                 110

Lys Ile Thr Ser Ala Leu Tyr Thr Leu Asn Phe Val Ser Gly Met Gln
            115                 120                 125

Phe Leu Ala Cys Ile Ser Ile Asp Arg Tyr Val Ala Thr Lys Val
        130                 135                 140

Pro Ser Gln Ser Gly Val Gly Lys Pro Cys Trp Ile Ile Cys Ser Cys
145                 150                 155                 160

Val Trp Met Ala Ala Ile Leu Leu Ser Ile Pro Gln Leu Val Phe Tyr
                165                 170                 175

Thr Val Asn Asp Asn Ala Arg Cys Ile Pro Ile Phe Pro Arg Tyr Leu
                180                 185                 190

Arg Thr Ser Met Lys Ala Leu Ile Gln Met Leu Glu Ile Cys Ile Gly
                195                 200                 205

Phe Val Val Pro Phe Leu Ile Met Gly Val Cys Tyr Phe Ile Thr Ala
        210                 215                 220

Arg Thr Leu Met Lys Met Pro Asn Ile Lys Ile Ser Arg Pro Leu Lys
225                 230                 235                 240

Val Leu Leu Thr Val Val Ile Val Phe Ile Val Thr Gln Leu Pro Tyr
                245                 250                 255

Asn Ile Val Lys Phe Cys Arg Ala Ile Asp Ile Ile Tyr Ser Leu Ile
                260                 265                 270

Thr Ser Cys Asn Met Ser Lys Arg Met Asp Ile Ala Ile Gln Val Thr
        275                 280                 285

Glu Ser Ile Ala Leu Phe His Ser Cys Leu Asn Pro Ile Leu Tyr Val
        290                 295                 300

Phe Met Gly Ala Ser Phe Lys Asn Tyr Val Met Lys Val Ala Lys Lys
305                 310                 315                 320

Tyr Gly Ser Trp Arg Arg Gln Arg Gln Ser Val Glu Glu Phe Pro Phe
                325                 330                 335

Asp Ser Glu Gly Pro Thr Glu Pro Thr Ser Thr Phe Ser Ile
                340                 345                 350

(2) INFORMATION FOR SEQ ID NO: 9:

(i) SEQUENCE CHARACTERISTICS:
        (A) LENGTH: 1273 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 429..1238

(x) PUBLICATION INFORMATION:
        (H) DOCUMENT NUMBER: US 60/053,693
        (I) FILING DATE: 25-JUL-1997

(xi) SEQUENCE DESCRIPTION: SEQ ID NO: 9:

GATGCATGCT CGAGCGGCCG CCAGTGTGAT GGATATCTGC AGAATTCGGC TTACTCACTA     60

TAGGGCTCGA GCGGCCGCCC GGGCAGGTCC CTCCAACAAG ACGCAGCACA GAGACACCA    120

CTACCTAACA CAGGCGACTC TGAGCACTCT CTCTCTGGGA CTGGGCAGAG CGGCAAACG    180
```

-continued

```
TCACCTCTCA GACAGCCTTT GACAGACAGG AGGTTCTACA TACCATGGGA GCCAGCCTG         240

TGTAAGATGG CCACCCTGAG CAATCACAAC CAGCTTGATC TTTCTAATGG CTCACACCC         300

GAGGAATACA AAATCGCAGC CCTAGTCTTC TACAGCTGCA TCTTCCTGAT TGGGCTGTT         360

GTTAATGTCA CTGCGTTGTG GGTTTTCAGC TGTACGACCA AGAAAAGAAC ACAGTGACC         420

TCTACATG ATG AAC GTT GCA CTA CTG GAC CTC GTA TTT ATA CTC AGT CTG         470
         Met Asn Val Ala Leu Leu Asp Leu Val Phe Ile Leu Ser     Leu
          1               5                  10

CCC TTT CGG ATG TTT TAC TAT GCA AAA GGC GAG TGG CCA TTT GGA GAG         518
Pro Phe Arg Met Phe Tyr Tyr Ala Lys Gly Glu Trp Pro Phe Gly Glu
 15              20                  25                  30

TAC TTC TGC CAC ATT CTT GGG GCC CTG GTG GTG TTT TAC CCA AGC CTC         566
Tyr Phe Cys His Ile Leu Gly Ala Leu Val Val Phe Tyr Pro Ser Leu
                 35                  40                  45

GCT CTG TGG CTT CTT GCT TTC ATT AGT GCT GAC AGA TAC ATG GCC ATC         614
Ala Leu Trp Leu Leu Ala Phe Ile Ser Ala Asp Arg Tyr Met Ala Ile
             50                  55                  60

GTA CAG CCA AAA TAT GCC AAG GAG CTG AAG AAC ACC GGC AAG GCC GTG         662
Val Gln Pro Lys Tyr Ala Lys Glu Leu Lys Asn Thr Gly Lys Ala Val
         65                  70                  75

CTT GCG TGT GGG GGG GTC TGG GTA ATG ACC CTG ACC ACC ACT GTC CCC         710
Leu Ala Cys Gly Gly Val Trp Val Met Thr Leu Thr Thr Thr Val Pro
     80                  85                  90

CTG CTA CTG CTC TAC GAA GAC CCA GAC AAT GCC TCC TCC CCG GCC ACC         758
Leu Leu Leu Leu Tyr Glu Asp Pro Asp Asn Ala Ser Ser Pro Ala Thr
 95                  100                 105                 110

TGC CTG AAG ATC TCC GAC ATC ACC CAC TTA AAA GCT GTC AAC GTG CTC         806
Cys Leu Lys Ile Ser Asp Ile Thr His Leu Lys Ala Val Asn Val Leu
                 115                 120                 125

AAC TTC ACG CGA CTC ATA TTT TTC TTC CTG ATC CCT TTG TTC ATC ATG         854
Asn Phe Thr Arg Leu Ile Phe Phe Phe Leu Ile Pro Leu Phe Ile Met
             130                 135                 140

ATC GGG TGC TAC GTG GTC ATC ATT CAC AGT CTC CTC CGA GGG CAG ACG         902
Ile Gly Cys Tyr Val Val Ile Ile His Ser Leu Leu Arg Gly Gln Thr
         145                 150                 155

TCT AAG CTG AAG CCC AAG GTC AAG GAG AAG TCC ATA CGG ATC ATC ATG         950
Ser Lys Leu Lys Pro Lys Val Lys Glu Lys Ser Ile Arg Ile Ile Met
     160                 165                 170

ACC CTC CTG CTG CAG GTG CTC GTC TGC TTC GTG CCC TTC CAC ATC TGC         998
Thr Leu Leu Leu Gln Val Leu Val Cys Phe Val Pro Phe His Ile Cys
175                 180                 185                 190

TTT GCC GTC CTG ATG CTA CAA GGA CAG GAG AAC AGC TAT AGC CCC TGG        1046
Phe Ala Val Leu Met Leu Gln Gly Gln Glu Asn Ser Tyr Ser Pro Trp
                 195                 200                 205

GGA GCC TTC ACC ACC TTC CTC ATG AAC CTC AGC ACC TGT CTC GAT GTA        1094
Gly Ala Phe Thr Thr Phe Leu Met Asn Leu Ser Thr Cys Leu Asp Val
             210                 215                 220

GTC CTC TAC TAC ATC GTT TCC AAA CAG TTC CAG GCT CGA GTC ATC AGC        1142
Val Leu Tyr Tyr Ile Val Ser Lys Gln Phe Gln Ala Arg Val Ile Ser
         225                 230                 235

GTC ATG CTG TAC CGC AAT TAC CTT CGC AGT GTT CGC AGA AAA AGT GTC        1190
Val Met Leu Tyr Arg Asn Tyr Leu Arg Ser Val Arg Arg Lys Ser Val
     240                 245                 250

CGA TCG GGC AGT TTA CGG TCA CTT AGC AAC ATG AAC AGT GAG ATG CTT        1238
Arg Ser Gly Ser Leu Arg Ser Leu Ser Asn Met Asn Ser Glu Met Leu
255                 260                 265                 270

TGAGTCAGAG CAAGCTGCCA GTCTTCAGTC TCTTT                                 1273
```

-continued (2) INFORMATION FOR SEQ ID NO: 10:

(i) SEQUENCE CHARACTERISTICS:
       (A) LENGTH: 270 amino acids
       (B) TYPE: amino acid
       (D) TOPOLOGY: linear (ii) MOLECULE TYPE: protein (xi) SEQUENCE DESCRIPTION: SEQ ID NO: 10:

```
Met Asn Val Ala Leu Leu Asp Leu Val Phe Ile Leu Ser Leu Pro Phe
 1               5                  10                  15

Arg Met Phe Tyr Tyr Ala Lys Gly Glu Trp Pro Phe Gly Glu Tyr Phe
                20                  25                  30

Cys His Ile Leu Gly Ala Leu Val Phe Tyr Pro Ser Leu Ala Leu
            35                  40                  45

Trp Leu Leu Ala Phe Ile Ser Ala Asp Arg Tyr Met Ala Ile Val Gln
    50                  55                  60

Pro Lys Tyr Ala Lys Glu Leu Lys Asn Thr Gly Lys Ala Val Leu Ala
65                  70                  75                  80

Cys Gly Gly Val Trp Val Met Thr Leu Thr Thr Val Pro Leu Leu
                85                  90                  95

Leu Leu Tyr Glu Asp Pro Asp Asn Ala Ser Ser Pro Ala Thr Cys Leu
                100                 105                 110

Lys Ile Ser Asp Ile Thr His Leu Lys Ala Val Asn Val Leu Asn Phe
            115                 120                 125

Thr Arg Leu Ile Phe Phe Leu Ile Pro Leu Phe Ile Met Ile Gly
130                 135                 140

Cys Tyr Val Val Ile Ile His Ser Leu Leu Arg Gly Gln Thr Ser Lys
145                 150                 155                 160

Leu Lys Pro Lys Val Lys Glu Lys Ser Ile Arg Ile Ile Met Thr Leu
                165                 170                 175

Leu Leu Gln Val Leu Val Cys Phe Val Pro Phe His Ile Cys Phe Ala
            180                 185                 190

Val Leu Met Leu Gln Gly Gln Glu Asn Ser Tyr Ser Pro Trp Gly Ala
        195                 200                 205

Phe Thr Thr Phe Leu Met Asn Leu Ser Thr Cys Leu Asp Val Val Leu
        210                 215                 220

Tyr Tyr Ile Val Ser Lys Gln Phe Gln Ala Arg Val Ile Ser Val Met
225                 230                 235                 240

Leu Tyr Arg Asn Tyr Leu Arg Ser Val Arg Arg Lys Ser Val Arg Ser
                245                 250                 255

Gly Ser Leu Arg Ser Leu Ser Asn Met Asn Ser Glu Met Leu
                260                 265                 270
```